US006013436A

United States Patent [19]
Hui et al.

[11] Patent Number: 6,013,436
[45] Date of Patent: *Jan. 11, 2000

[54] COMPOSITIONS AND METHODS FOR DIAGNOSIS OF MUTATION IN THE VON HIPPEL-LINDAU TUMOR SUPPRESSOR GENE

[75] Inventors: May Hui, Toronto; James M. Dunn, Scarborough; John K. Stevens, Toronto; Denis Capatos, Waterloo; David E. Matthews, Kitchener, all of Canada

[73] Assignee: Visible Genetics, Inc., Toronto, Canada

[*] Notice: This patent is subject to a terminal disclaimer.

[21] Appl. No.: 08/699,628

[22] Filed: Aug. 19, 1996

Related U.S. Application Data

[63] Continuation of application No. 08/583,289, Jan. 5, 1996, abandoned, which is a continuation-in-part of application No. 08/271,946, Jul. 8, 1994, Pat. No. 5,545,527, and application No. 08/388,381, Feb. 14, 1995, Pat. No. 5,552,283.

[51] Int. Cl.⁷ .............................. C12Q 1/68; C12P 19/34; C07H 21/04
[52] U.S. Cl. .......................... 435/6; 435/91.2; 536/23.5; 536/23.1; 536/24.33; 536/24.31
[58] Field of Search ..................... 435/6, 91.2; 536/23.1, 536/24.31, 24.32, 23.5

[56] References Cited

U.S. PATENT DOCUMENTS

| | | | |
|---|---|---|---|
| 5,545,527 | 8/1996 | Stevens et al. | 435/6 |
| 5,552,283 | 9/1996 | Diamandis et al. | 435/6 |
| 5,654,138 | 8/1997 | Lerman et al. | 435/6 |

FOREIGN PATENT DOCUMENTS

| | | |
|---|---|---|
| 9426894 | 11/1994 | WIPO . |
| 9601908 | 1/1996 | WIPO . |
| 9601909 | 1/1996 | WIPO . |
| 9607761 | 3/1996 | WIPO . |

OTHER PUBLICATIONS

GenBank Report, Accession No. L15409 (1993).
GenBank Report, Accession No. U19763 (1995).
Listing of DNA Sequences for VHL cDNA, exon probes and intron probes found in the Genome Data Base™ as of Nov. 3, 1995.
Listing of DNA Sequences for VHL intron primers found in the Genome Data Base™ as of Nov. 3, 1995, and map showing positions relative to Sequences shown in application.
Travis, J., "New Tumor Suppressor Gene Captured", *Science* 260: 1235 (1993).
Latif et al., "Identification of the von Hippel–Lindau Disease Tumor Suppressor Gene", *Science* 260: 1317–1320 (1993).
Richards et al., "Mapping the Von Hippel–Lindau disease tumour suppressor gene: identification of germline deletions by pulsed field gel electrophoresis", *Hum. Molec. Gen.* 2: 879–882 (1993).
Gnarra et al., "Mutations of the VHL tumour suppressor gene in renal carcinoma" *Nature Genetics* 7: 85–90 (1994).
Chen et al.., "Germline Mutations in the von Hippel–Lindau Disease Tumor Suppressor Gene: Correlations with Phenotype", *Human Mutation* 6: 66–75 (1995).
Kuzmin et al., "Identification of the promoter of the human von Hippel–Lindau disease tumor suppressor gene", *Oncogene* 10: 2185–2194 (1995).
Duan et al., "Inhibition of Transcription Elongation by the VHL Tumor Suppressor Protein", *Science* 269: 1402–1406 (1995).
Orita et al., "Detection of polymorphisms of human DNA by gel electrophoresis as single–stranded polymorphisms" *Proc. Nat'l Acad. Sci. (USA)* 86: 2766–2770 (1989).
Rychlik, W. "Selection of Primers for Polymerase Chain Reaction", *Meth. Molec. Biol.* 15: 31–40 (1993).
Shimizu et al., "Detection of Mutations of the RB1 Gene in Retinoblastoma Pateitns by Using Exon–by–Exon PCCR–SSCP Analysis", *Am. J. Hum. Genet.* 54: 793–800 (1994).
Lohmann et al., "Detection of small RB1 gene deletions in retinoblastoma by multiplex PCR and high–resolution gel electrophoresis" *Hum. Genet.* 89: 49–53 (1992).
Breslauer et al., "Predicting DNA duplex stability from the base sequence", *Proc. Nat'l Acad. Sci. (USA)* 83: 3746–3750 (1986).
Chamberlain et al., "Detection of Gene Deletions using Multiplex Polymerase Chain Reactions", *Meth. Molec. Biol.* 9: 299–312.
Dunn et al., "Sequence Based Diagnosis of Retinoblastoma", *J. Cellular Biochem.* Supp 18C: 199 (1994).
Sun et al., "The von Hippel–Lindau (VHL) disease tumor–suppressor gene is not mutated in nasopharyngeal carcinomas" *Int. J. Cancer* 60: 437–438 (1995).
Decker et al., "Molecular and Cytogenetic Studies on Sproadic and Familial Forms of Renal Cell Carcinomas", *Cancer Genet. Cytogenet.* 84: 130 (1995).
Latif et al. Science 260: 1317–1320, 1993.

*Primary Examiner*—Carla J. Myers
*Attorney, Agent, or Firm*—Oppedahl & Larson LLP

[57] ABSTRACT

The instant invention relates to methods and products for the diagnosis of mutations in the von Hippel-Lindau tumor suppressor gene. More specifically, the products are DNA oligonucleotides for use in amplifying and sequencing genomic DNA and kits including these oligonucleotides. The method of the invention relates to a hierarchical system for cost-effective diagnosis of von Hippel-Lindau tumor suppressor disease-associated mutations.

24 Claims, 10 Drawing Sheets

Fig. 2

|  | HIERARCHICAL | SEQUENCE-BASED CURRENT METHOD |
|---|---|---|
| SAMPLES | 100 | 100 |
|  | $10/IMMUNOASSAY x 100 = $1,000 |  |
|  | $25/PROBE x 80 = $2,000 |  |
|  | $80/FRAG. ANAL. x 65 = $5,200 |  |
|  | $500/DNA SEQ. x 35 = $7,500 | $500/DNA SEQ. x 100 = $50,000 |
| TOTALS | $25,700 | $50,000 |

Fig. 4

| Test # | TECHNIQUE |  |
|---|---|---|
| 1 | FRAGMENT ANALYSIS | POOL A |
| 2 | FRAGMENT ANALYSIS | POOL B |
| 3 | FRAGMENT ANALYSIS | POOL C |
| 4 | DNA SEQUENCING | EXON 2 |
| 5 | DNA SEQUENCING | EXON 1 |
| 6 | DNA SEQUENCING | EXON 3 |

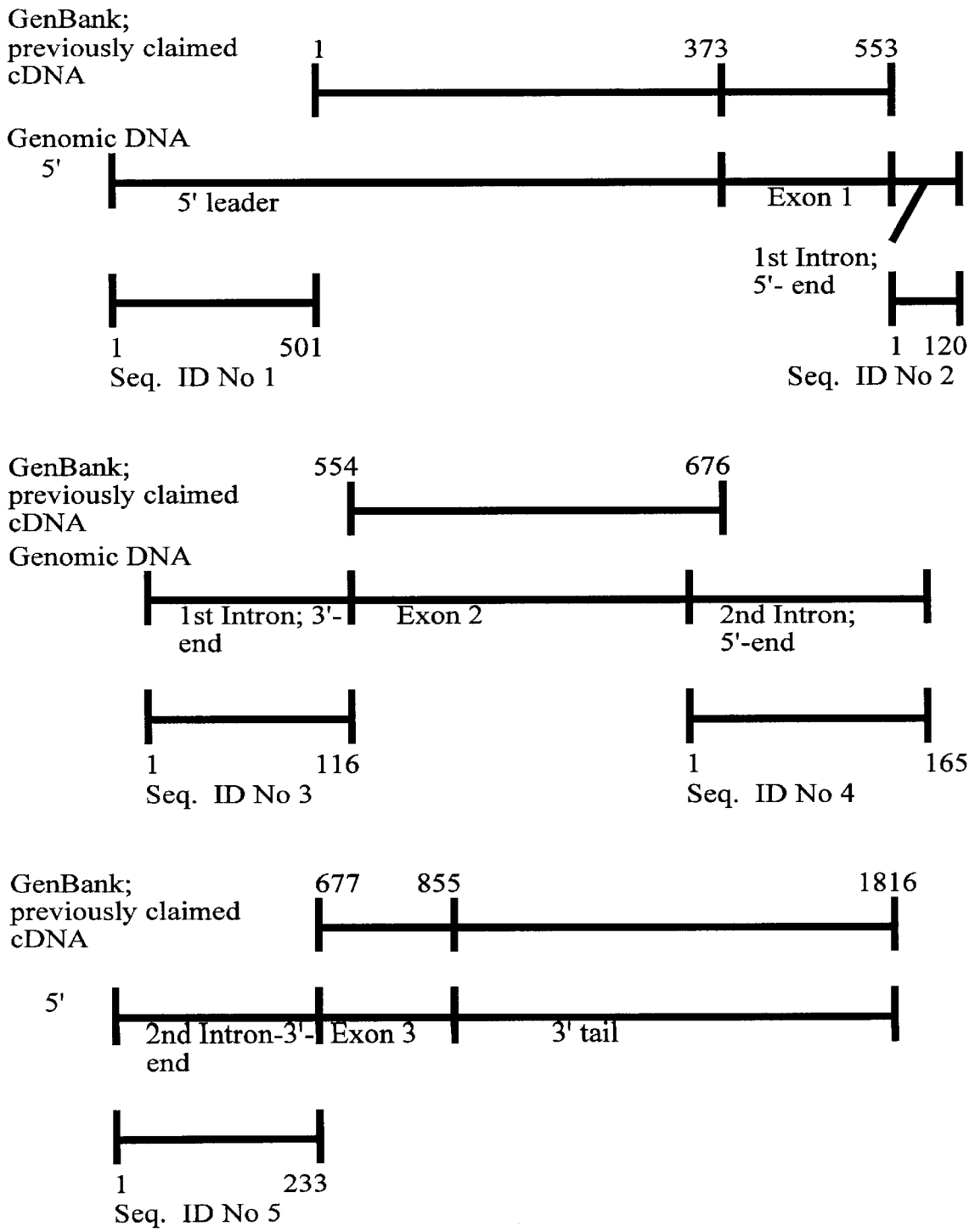

FIG. 3B

[SEQ ID NO: 1]

Location: 5' leader/contiguous to 5'end of disclosed cDNA.

```
1   gaattcagtt agttgacttt ttgtacttta taagcgtgat gattgggtgt tcccgtgtga
61  gatgcgccac cctcgaacct tgttacgacg tcggcacatt gcgcgtctga catgaagaaa
121 aaaaaaattc agttagtcca ccaggcacag tggctaaggc ctgtaatccc tgcactttga
181 gaggccaagg caggaggatc acttgaaccc aggagttcga gaccagccta ggcaacatag
241 cgagactccg tttcaaacaa caaataaaaa taattagtcg ggcatggtgg tgcgcgccta
301 cagtaccaac tactcgggag gctgaggcga gacgatcgct tgagccaggg aggtcaaggc
361 tgcagtgagc caagctcgcg ccactgcact ccagcccggg cgacagagtg agaccctgtc
421 tccaaaaaaa aaaaaaaaca ccaaacctta gagggtgaa aaaaattt atagtggaaa
481 tacagtaacg agttggccta g
```

[SEQ ID NO: 2]

Location: First Intron 5' end/ contiguous to 3' end of exon 1

```
1   (AG)gtacggg cccggcgctt aggcccgacc cagcaggacg atagcacggt ctaagcccct
58  ctaccgcccc ggggtccatt cagacgggga actaggcccc ttgaggcagg acacatccag
118 ggt
```

[SEQ ID NO: 3]

Location: First Intron 3' end/ contiguous to 5' end of exon 2

```
1   ctcctgacct ctatgatccg cctgcctcgg cctccaaagt gctgggatta caggtgtggg
61  ccaccgtgcc cagccaccgg tgtgggctct ttaacaacct ttgcttgtcc cgatag (GT)
```

[SEQ ID NO: 4]

Location: Second Intron 5' end/ contiguous to 3'end of exon 2

```
1    (AG) g tactgacgtt ttactttta aaagataag gttgttgtgg taagtacagg
52  atagaccact tgaaaaatta agcccagttc tcaattttg cctgatgtca ggcacggtat
112 ccaatctttt tgtatcctat tctctaccat aaataaaatg gaagtgatga tttt
```

[SEQ ID NO: 5]

Location: Second Intron 3' end/ contiguous to 5' end of exon 3]

```
1   ctacagaagg catgaacacc atgaagtgtc catagggggcc acagcataca cactgccaca
61  tacatgcact cactttttt ctttaaccta aaagtgaaga tccatcagta gtacaggtag
121 ttgttggcaa aagcctcttg ttcgttcctt gtactgagac cctagtctgc cactgaggat
181 ttggttttg cccctagtc tgccactgag gatttggttt
ttgcccgttc cag (TG)
```

VHL cDNA in GenBank; previously claimed

Important Loci

```
(497/501=)1cctcgcctcc gttacaacag cctacggtgc tggaggatcc ttgtgcgcac gcgcacagcc
         61 tccggccggc tatttccgcg agcgcgttcc atcctctacc gagcgcgcgc gaagactacg
        121 gaggtcgact cgggagcgcg cacgcagctc cgcccgcgt  ccgacccgcg gatcccgcgg
        181 cgtccggccc gggtggtctg gatcgcggag ggaatgcccc ggagggcgga gaactgggac
        241 gaggccgagg taggcgcgga ggaggcaggc gtcgaagagt acggccctga agaagacggc
        301 ggggaggagt cgggcgccga ggagtccggc ccggaagagt ccggcccgga ggaactgggc
        361 gccgaggagg ag[Exo1]atggaggc cgggcggccg cggcccgtgc tgcgctcggt gaactcgcgc
        421 gagccctccc aggtcatctt ctgcaatcgc agtccgcgcg tcgtgctgcc cgtatggctc
        481 aacttcgacg gcgagccgca gccctaccca acgctgccgc ctggcacggg ccgccgcatc
        541 cacagctacc gag[Exo2]gtcacct ttggctcttc agagatgcag ggacacacga tgggcttctg
        601 gttaaccaaa ctgaattatt tgtgccatct ctcaatgttg acggacagcc tattttgcc
        661 aatatcacac tgccag[Exo3]tgta tactctgaaa gagcgatgcc tccaggttgt ccggagccta
        721 gtcaagcctg agaattacag gagactggac atcgtcaggt cgctctacga agatctggaa
        781 gaccacccaa atgtgcagaa agacctggag cggctgacac aggagcgcat tgcacatcaa
        841 cggatgggag attga[end]agatt tctgttgaaa cttacactgt ttcatctcag cttttgatgg
        901 tactgatgag tcttgatcta gatacaggac tggttccttc cttagtttca aagtgtctca
        961 ttctcagagt aaaataggca ccattgctta aagaaagtt  aactgacttc actaggcatt
       1021 gtgatgttta ggggcaaaca tcacaaaatg taatttaatg cctgcccatt agagaagtat
       1081 ttatcaggag aaggtggtgg cattttgct  tcctagtaag tcaggacagc ttgtatgtaa
       1141 ggaggtttat ataagtaatt cagtgggaat tgcagcatat cgtttaattt taagaaggca
       1201 ttggcatctg cttttaatgg atgtataata catccattct acatccgtag cggttggtga
       1261 cttgtctgcc tcctgctttg ggaagactga ggcatccgtg aggcagggac aagtctttct
       1321 cctctttgag acccagtgc  ctgcacatca tgagccttca gtcagggttt gtcagaggaa
       1381 caaaccaggg gacactttgt tagaaagtgc ttagaggttc tgcctctatt tttgttgggg
       1441 ggtgggagag gggaccttaa aatgtgtaca gtgaacaaat gtcttaaagg gaatcatttt
       1501 tgtaggaagc attttttata attttctaag tcgtgcactt tctcggtcca ctcttgttga
       1561 agtgctgttt tattactgtt tctaaactag gattgacatt ctacagttgt gataatagca
       1621 ttttgtaac  ttgccatccg cacagaaaat acgagaaaat ctgcatgttt gattatagta
       1681 ttaatggaca aataagtttt tgctaaatgt gagtatttct gttcctttt  gtaaatatgt
       1741 gacattcctg attgatttgg gtttttttgt tgttgttgtt ttgtttttgtt ttgtttttt
       1801 gggatggagg [gaattc (6 nts added at 3'end in patent application)]
```

GenBank Accession No. L15409

FIG. 3C

Location of Amplification Primers

Location of Sequencing Primers

COMPOSITIONS AND METHODS FOR DIAGNOSIS OF MUTATION IN THE VON HIPPEL-LINDAU TUMOR SUPPRESSOR GENE

RELATED APPLICATIONS

This application is a continuation of U.S. patent application Ser. No. 08/583,289 filed Jan. 5, 1996, now abandoned which is a continuation-in-part of U.S. patent application Ser. No. 08/271,946, filed Jul. 8, 1994 now U.S Pat. No. 5,545,527 and of, U.S. patent application Ser. No. 08/388,381, filed Feb. 14, 1995 now U.S. Pat. No. 5,552,283, said U.S. patent applications corresponding to PCT/US95/08605 and PCT/US95/08606, the teachings of which are incorporated herein by reference.

FIELD OF INVENTION

The instant invention relates to methods and compositions for the diagnosis of mutations in the von Hippel-Lindau tumor suppressor gene. More specifically, the compositions relate to DNA oligonucleotides for use in amplifying and sequencing genomic DNA. The method of the invention relates to a hierarchical system for the cost-effective diagnosis of von Hippel-Lindau tumor suppressor disease-associated mutations.

BACKGROUND OF THE INVENTION

The von Hippel-Lindau (VHL) disease is a familial cancer syndrome that is dominantly inherited and that predisposes affected individuals to a variety of tumors. The minimum birth incidence of VHL disease is low, being one in 36,000, but the consequence of the disorder is serious in that median actuarial life expectancy is 49 years. In 1993, a gene discovered by positional cloning at human chromosome 3p25-56 was identified as the VHL disease tumor suppressor gene (Latif, F., Tory, K., Gnarra, J., et al. "Identification of the von Hippel-Lindau Disease Tumor Suppressor Gene." Science 260, 1317–1320 (1993)). The cDNA sequence of this gene is the subject of U.S. patent application Ser. No. 08/061,889 U.S. Pat. No. 5,654,138.

In 1994, a related group reported that VHL mutations could be found in a majority of localized and advanced sporadic renal carcinomas. (Gnarra, J. R., Tory, K., Weng, Y. et al. "Mutations of the VHL Tumour Suppressor Gene in Renal Carcinoma". Nature Genetics 7, 85–90 (1994)). This finding substantially widened the scope of clinical interest in the VHL tumor suppressor gene because over 60,000 persons per year in North America alone are diagnosed with kidney growths such as cysts and neoplasms. The detection of VHL gene mutation in biopsies of such growths is therefore diagnostic of a developing tumor, and only those with VHL mutation are thought to be malignant.

Of equal importance, is the finding also reported by Gnarra et al. that of 119 tumors taken from 11 different tissues outside the kidney, not one demonstrated VHL mutation. Such a finding is decisive in determining if a neoplasm is a secondary metastatic tumour of the kidney, or not.

Further information on von Hippel-Lindau disease can be found in the National Cancer Institute, CancerNet database accession number 193300. (http://www.ncc.go.jp/cnet.html).

The cDNA sequence for the von Hippel-Lindau tumor suppressor gene can be obtained from the On-line Mendelian Inheritance in Man database (http://gdbwww.gdb.org/omimdoc/omimtop.htm] GDB ID: G00-120-488; and also in GenBank (http://golgi.harvard.edu/genbank.html) accession number L15409. GenBank also contains sequence disclosed in a recent publication covering the 5' non-translated sequence preceding the initiation codon of the mRNA for the VHL gene. (Kuzmin,I., Duh,F., Latif,F., Geil, L., Zbar,B. and Lerman, M. I. "Identification of the promoter of the human von Hippel Lindau disease tumor suppressor gene" Oncogene 10, 2185–2194 (1995)).

Fragments of various intron sequences can be obtained from the GenBank database G00-361-137; G00-361-147; G00 361-151; G00 375-126; G00 375-133; G00-375-187; G00-375-193; G00-437-732; G00-532-940; G00-532-957; G00-532-965. These sequences have been used as amplification primers for RFLP analysis. However, the intron sequences set out in this application for the purpose set out in this application have not been published.

Methods for identifying VHL tumor suppressor gene mutations have been disclosed in the above noted publications and patent applications. While these methods have had some success in small scale sampling, as demonstrated in the above noted publications, they suffer from practical and theoretical shortcomings. In particular, nucleic acid assays, using cDNA sequences, cannot find mutations in the introns or at the intron/exon boundary of genomic DNA because convenient amplification of such regions requires at least one primer from within the region. Without having at least a small part of the intron amplified, it is impossible to obtain the crucial DNA sequence information by conventional means. Further, mRNA and cDNA are not necessarily the preferred molecules for diagnosis, if genomic DNA is available. This flows from the fact that intact mRNA is often difficult to obtain from patient samples, while genomic DNA sufficient for analysis can usually be obtained even from very small patient samples. Another shortcoming is that one of the most commonly used methods for diagnosing VHL tumor suppressor gene mutations, Southern blot probing, is time consuming and does not lend itself to use in a rapid or low cost diagnostic laboratory.

Currently, no laboratory in the world performs routine VHL mutation diagnostic assays for large numbers of patients. One of the reasons for this is the inability to determine a low cost, high sensitivity and high specificity methodology for routine diagnostic testing of VHL tumor suppressor gene mutations. It is therefore highly desirable to have an improved diagnostic method for the presence or absence of VHL mutation. In particular it would be convenient to develop a diagnostic hierarchical system which could take advantage of the new generation of high speed automated DNA sequencing apparatuses, such as the instruments disclosed in U.S. patent application Ser. No. 08/332,577 now U.S. Pat. No. 5,627,022; Ser. No. 08/353,932, now U.S. Pat. No. 5,507,934; Ser. Nos. 08/332,892; 08/387,272 now U.S. Pat. No. 5,543,018, incorporated herein by reference, which can determine 300 nucleotides (nt) of a sequenced gene in under half and hour. Such a diagnostic hierarchical system is disclosed in the parent application of the instant application, U.S. patent application Ser. No. 08/271,946 now U.S. Pat. No. 5,545,527.

The instant invention provides a low cost, high sensitivity and high specificity methodology for routine diagnostic testing of VHL tumor suppressor gene mutations. It provides intron based primers and combinations of primers which simplify the work of the diagnostic technician. Intron sequences have not previously been used for routine diagnosis of VHL mutations for a number of reasons. First, the sequences themselves have not been known. Second, intron sequences have been expected to show a degree of variability which would make them unreliable for diagnosis. Third, no one had developed an efficient method for using combinations of primers derived from intron sequences.

It is an object of the instant invention to provide a rapid and cost-effective diagnostic hierarchical system for determining the presence or absence of mutation in the VHL gene of a plurality of patients.

It is a further object of the instant invention to provide oligonucleotides from intron regions of the genomic VHL tumor suppressor gene (at human chromosome 3p25-p26) that can be used for the diagnosis of VHL tumor suppressor gene mutation.

It is a further object of the instant invention to provide oligonucleotides from the 5' leader sequence of the genomic VHL tumor suppressor gene (at human chromosome 3p25-p26) that can be used for the diagnosis of VHL tumor suppressor gene mutation.

It is a further object of the instant invention to provide oligonucleotide primers from the regions immediately flanking the intron/exon boundaries of the genomic VHL tumor suppressor gene (at human chromosome 3p25-p26) that can be used for the diagnosis of VHL tumor suppressor gene mutation.

It is a further object of the instant invention to provide kits for the diagnosis of VHL tumor suppressor gene mutation containing these oligonucleotides.

SUMMARY OF INVENTION

The present invention includes purified oligonucleotides for use as amplification and sequencing primers in the diagnosis of VHL tumor suppressor gene mutation. The primers are designed to hybridize with a patient's genomic DNA, particularly in the flanking intron regions adjacent to the exons of the VHL tumor suppressor gene. Particularly preferred primers constitute sets that are compatible for co-amplification and that produce amplified DNA fragments of distinctive lengths from other fragments amplified in the same set. Preferred primers are from 18 to 23 nucleotides in length, without internal homology or primer—primer homology.

The primers are selected from one of the following intron sequences and their complements. The sequences set forth below are SEQ ID NO:1 through SEQ ID NO:5:

[SEQ ID NO:1]

Location: 5' leader/contiguous to 5' end of disclosed cDNA.

1   gaattcagtt agttgacttt ttgtacttta taagcgtgat gattgggtgt tcccgtgtga 61  gatgcgccac cctcgaacct tgttacgacg tcggcacatt gcgcgtctga catgaagaaa 121 aaaaaaattc agttagtcca ccaggcacag tggctaaggc ctgtaatccc tgcactttga 181 gaggccaagg caggaggatc acttgaaccc aggagttcga gaccagccta ggcaacatag 241 cgagactccg tttcaaacaa caaataaaaa taattagtcg ggcatggtgg tgcgcgccta 301 cagtaccaac tactcgggag gctgaggcga gacgatcgct tgagccaggg aggtcaaggc 361 tgcagtgagc caagctcgcg ccactgcact ccagcccggg cgacagagtg agacctgtc 421 tccaaaaaaa aaaaaaaaca ccaaaccttta gagggtgaa aaaaaatttt atagtggaaa 481 tacagtaacg agttggccta g

[SEQ ID NO:2]

Location: First Intron 5' end/ contiguous to 3 end of exon 1

1   (AG)gtacggg cccggcgctt aggcccgacc cagcaggacg atagcacggt ctaagcccct 58  ctaccgcccc ggggtccatt cagacgggga actaggcccc ttgaggcagg acacatccag 118 ggt

[SEQ ID NO:3]

Location: First Intron 3' end/ contiguous to 5' end of exon 2

1   ctcctgacct ctatgatccg cctgcctcgg cctccaaagt gctgggatta caggtgtggg 61  ccaccgtgcc cagccaccgg tgtgggctct ttaacaacct ttgcttgtcc cgatag (GT)

[SEQ ID NO:4]

Location: Second Intron 5' end/ contiguous to 3' end of exon 2

1   (AG) g tactgacgtt ttactttta aaaagataag gttgttgtgg taagtacagg 52  atagaccact tgaaaaatta agcccagttc tcaatttttg cctgatgtca ggcacggtat 112 ccaatctttt tgtatcctat tctctaccat aaataaaatg gaagtgatga tttt

[SEQ ID NO:5]

Location: Second Intron 3' end/contiguous to 5' end of exon 3]

-continued

```
1   ctacagaagg catgaacacc atgaagtgtc catagggggcc acagcataca cactgccaca 61  tacatgcact cacttttttt ctttaaccta aaagtgaaga tccatcagta gtacaggtag 121 ttgttggcaa aagcctcttg ttcgttcctt gtactgagac cctagtctgc cactgaggat 181 ttggtttttg cccctagtc tgccactgag gatttggttt ttgcccgttc cag (TG)
```

The abbreviations used for the nucleotides are those used standardly in the art.

These primers may be provided in a kit with other reagents for the diagnosis of VHL tumor suppressor gene mutation. The kit comprises oligonucleotides useful as primers in PCR or another amplification reaction for VHL tumor suppressor gene mutation.

In a further aspect of the present invention, rapid and cost effective diagnosis of VHL tumor suppressor gene mutation in a plurality of patients is achieved by a diagnostic hierarchical system comprising a plurality of diagnostic tool of increasing sensitivity, of increasing cost, in which each tool has high specificity. The first steps in the hierarchical system may include low sensitivity and lower specificity techniques which, because of their relatively low cost, help reduce the overall cost of the diagnostic test. The final assay in the hierarchical system is selected to provide a highly sensitive and highly specific test for the existence of the disease associated mutation. Intermediate tests of progressively greater accuracy may also be included in the hierarchical system. The hierarchical system comprises selecting diagnostic tests for mutations in the VHL tumor suppressor gene from a group including:

(a) analysis of genomic DNA from a patient sample by quantitative amplification of at least one VHL tumor suppressor gene exon using amplification primers complementary to intron regions flanking each exon and examination of the length or quantity of each amplified fragment for nucleotide insertions or deletions or quantitative changes relative to the normal VHL tumor suppressor gene. Preferably, the amplification primers are multiplexed so that more than one DNA fragment is amplified in a single vessel, using sets of primers which provide gene fragments of distinctive lengths when used to amplify a normal VHL tumor suppressor gene;

(b) other genetic analysis of genomic DNA by using PCR-SSCP, Southern blot analysis, probe-based testing; CLEAVASE™ digestion; and (c) analysis of genomic DNA from a patient sample by sequencing of the VHL tumor suppressor gene beginning with the sequencing of those regions most likely to harbor point mutations, and proceeding to sequence regions less likely to harbor point mutations using the introns of this invention.

Once the hierarchical system has been selected, the individual patient samples are analyzed first using the lowest sensitivity/lowest cost assay in the hierarchical system. If the result of the first assay is negative for the presence of a disease-associated mutation, then the next assay in the hierarchical system is performed. This process is repeated until the final assay has been performed on all samples which gave negative results when tested by all less-sensitive assays in the hierarchical system.

The present invention further provides a mechanism for evaluating possible assays to define an optimal or near-optimal diagnostic algorithm made up of known testing procedures for the VHL disease tumor suppressor gene which optimizes overall performance while minimizing costs. The selection of an optimal or near-optimal diagnostic algorithm includes a consideration of the cost of each test as well as the sensitivity and specificity of the tests.

In accordance with the invention, the first step in the process is calibration of the available tests for a given genetic mutation to establish a relative sensitivity, specificity and cost for each available test. Each possible combination of tests up to a pre-defined maximum number of tests is then evaluated to determine the overall sensitivity, overall specificity, the predictive value of a positive test and the predictive value of a negative test. For those combinations where these values all exceed a threshold level of reliability, the expected cost of performing the test, $E[C_A]$ is given by the equation $$E[C_n] = \sum_{r=1}^{n}\left(\rho_{\Pi e}\sum_{j=1}^{r} C_{\gamma \varpi \Delta}\right)$$

where $\rho_{A,r}$ is the probability that a given number of tests (r) will have to be performed to achieve an unambiguous answer, $C_{(j)}$ is the cost of each test j in the algorithm, and the summation from j=1 to r is the sum of the cost for the first r tests in the algorithm.

Once the hierarchy has been selected for diagnosis of the VHL tumor suppressor gene, the patient sample is analyzed first using the lowest assay in the hierarchical system. If the result of the first assay is negative for the presence of a disease-associated mutation, then the next assay in the hierarchy is performed. If the result is positive, subsequent assays in the hierarchical system may or may not be performed depending on the specificity of the first assay as defined within the diagnostic algorithm. This process is repeated until the final assay has been performed on all samples which gave negative or ambiguous results when tested by all less-sensitive assays in the hierarchical system.

A major advantage of this hierarchical system is the ability to dramatically reduce the per-sample cost of targeted genetic screening and diagnosis for VHL tumor suppressor gene mutations. By utilizing assays of progressively greater sensitivity and cost only when the increased sensitivity is actually needed, and by selecting a diagnostic algorithm that takes into account the inherent strengths and weaknesses of available tests, the reliability which was thought to be available only by extremely costly sequence-based diagnosis can be achieved at average per-patient costs that are a fraction of the cost normally associated with performing a sequence-based diagnosis.

A further aspect of the instant invention discloses a cost-effective method for diagnosing VHL tumor suppressor gene mutations in family members of an individual diagnosed as carrying a germ-line VHL mutation. In this method only the specific mutation identified in the diagnosed individual is sought in the family members.

BRIEF DESCRIPTION OF THE FIGURES

FIG. 2 shows a cost evaluation comparing the cost of a four-level hierarchical system of the type shown in FIG. 1 to the cost of using sequence based diagnosis on all individuals.

FIG. 3(a) is a map of VHL Tumor Suppressor Gene. FIG. 3(b) provides the sequences of intron DNA nucleotides of SEQ ID NO:1 through SEQ ID NO:5. Sequences of intron DNA nucleotides are adjacent to the exons of the VHL gene. The nucleotides which are found in the VHL cDNA (GenBank accession No. L15409) are denoted above the middle line, while nucleotides of the listed sequences are below the line. FIG. 3(c) provides VHL cDNA (GenBank Accession No. L15409).

FIG. 4 shows a preferred hierarchical system suitable for diagnosis and targeted screening for mutations in the VHL tumor suppressor gene.

DETAILED DESCRIPTION OF THE INVENTION

Figure 1:
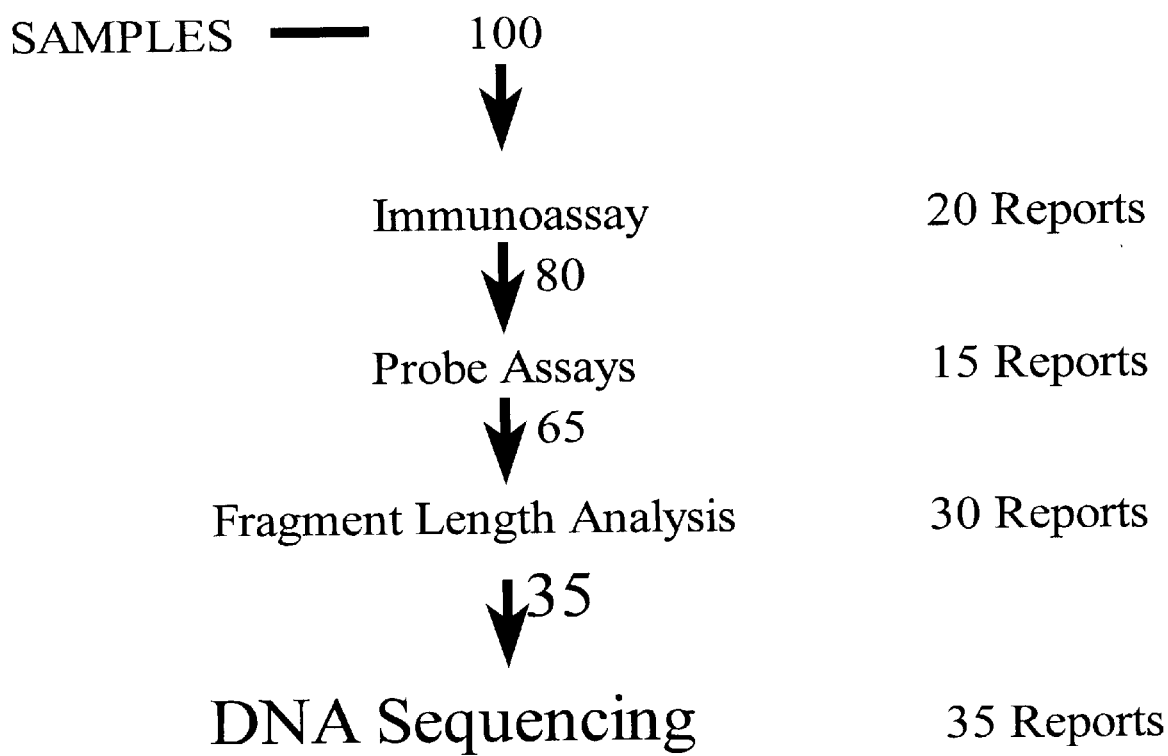
FIG. 1 is a schematic representation of a four-level hierarchical system according to the invention.

The present invention involves the use of a structured diagnostic approach to the identification of VHL tumor suppressor disease-associated mutations in a plurality of patients. The present invention utilizes the hierarchical system which is disclosed generally in U.S. patent application Ser. No. 08/271,946 filed Jul. 8, 1994, now U.S. Pat. No. 5,545,527, U.S. patent application Ser. No. 08/388,381, now U.S. Pat. No. 5,552 283, and U.S. patent applications corresponding to PCT/US95/08605 and PCT/US95/08606 which are incorporated herein by reference. The fundamental concept of the invention is the utilization of a testing hierarchical system composed of a plurality of assays of increasing sensitivity (and thus generally of increasing cost) as a targeted screening or diagnostic method for evaluation of a plurality of patients. The assay having the lowest sensitivity in the hierarchical system is applied to all samples submitted for testing. If a positive result is obtained in the first assay, a report is made indicating a positive result for the sample. If a negative result is obtained, the sample is tested using an assay having a greater sensitivity than the one just used in the hierarchical system. This hierarchical system is repeated until the highest level of sensitivity in the hierarchical system has been reached.

Description of Terms

As used in the specification and claims of this application, the term "VHL tumor suppressor gene" refers to a genomic DNA sequence which encodes a polypeptide for the von Hippel-Lindau tumor suppressor protein (the polypeptide being known as the "VHL gene product"). The VHL tumor suppressor gene is sometimes known as the "VHL disease gene" or the "VHL gene".

As used herein, the term "VHL tumor suppressor disease-associated mutation" refers to any mutations of a patient's genomic DNA which lead to a non-functioning or defective VHL gene product or to the failure to produce any VHL gene product from the mutated VHL gene. Such mutations may be point mutations (i.e., mutations in which one or more bases within the nucleic acid sequence have been replaced by a different base), insertion mutations (i.e., mutations in which the total length of the gene of interest has been increased by the insertion of one or more bases), deletion mutations (mutations in which the total length of the gene of interest has been decreased by removal of one or more bases) and inversion mutations (mutations in which a region of two or more bases has been rotated 180 degrees), or combinations of these mutations.

As used herein, the term "specificity" relates to the incidence of false positive results in a particular test. A test which has "high specificity" has fewer than 1% false positive results, and thus rarely, if ever, gives an erroneous indication that a mutation is present, but may fail to detect the mutation in some or even many instances. In contrast, the term "sensitivity" relates to the incidence of false negative results. A test which has "high sensitivity" has fewer than 1% false negative results, and thus will rarely if ever miss the presence of a mutation, although it may provide an incorrect diagnosis for the presence of the mutation. Tests with high specificity and sensitivity, for example with an error rate of less than 0.1% may of course be used if the benefits of the better performance warrant the cost of such tests.

As used herein, the term "targeted screening" refers to screening tests performed on individuals who as a result of family relationship, exposure to hazardous environments or other factors have been identified as being within a risk group for a particular form of genetic disease.

As used herein, the term "body sample" includes blood sample, tissue biopsy sample, excretion or secretion, or other tissue sample collected from an individual.

As used herein, the term "wild-type" in reference to a gene refers to the gene and any variation of that gene (allele) found in the general population which is thought to function normally and is not associated with a disease condition.

As used herein, the word "diagnosis" or "diagnostic" refers to the identification of the presence or absence of a condition, in this case the VHL tumor suppressor disease-associated mutation. A diagnosis may be that there is no mutation, or that no mutation is found in the body sample.

Hierarchical System

The tests forming the hierarchical system in accordance with the invention are selected from among tests of high specificity, where the sensitivity of the tests gets progressively greater. The tests which are selected for the hierarchical system depend on a number of factors. To illustrate the selection criteria for the tests within the hierarchical system, several representative examples will be considered.

FIG. 1 shows a suitable hierarchical system for use in testing for a VHL tumor suppressor disease-associated mutation that results in the production of a defective gene product. As shown, the samples from a plurality of patients are first tested for a disease-associated mutation in a gene of interest by first performing an immunoassay on a portion of the sample obtained from each patient. Such a test will generally be selected to provide a positive reaction in the presence of gene-product of a mutant gene. The immunoassay is selected to be highly specific such that any positive result is a reliable indicator of the existence of the disease-associated mutation, but need not be highly accurate.

Samples from patients that had negative immunoassay results are next tested using a probe-based assay. In an Allele Specific Oligonucleotide Assay ("ASO"), the probe-based assay will utilize at least one oligonucleotide probe which specifically and selectively hybridizes with the VHL tumor suppressor gene in its mutated form. Thus, the formation of a duplex nucleic acid hybrid containing the nucleic acid probe is indicative of the presence of the mutation in the VHL tumor suppressor gene. Again, because of the high specificity of probe-based tests, any positive result may be relied upon as an indicator of the presence of the disease-associated mutation.

Samples in which mutations are still not identified are next subjected to fragment length analysis. Fragments of each patient's genomic DNA are amplified with VHL tumor suppressor gene intron specific primers. The amplified regions of the VHL tumor suppressor gene therefore include the exon of interest, the splice site junction at the exon/intron boundaries, and a short portion of intron at either end of the amplification product. The lengths of the amplified fragments are compared to known and expected standard lengths from the wild-type gene to determine if an insertion or deletion mutation is found in the patient sample. VHL tumor suppressor gene mutation may be diagnosed if such length variations are identified.

Samples for which the immunoassay, probe-based assay and fragment analysis assay are negative, are further analyzed in accordance with the invention by determining the sequence of DNA in at least a selected region of the VHL tumor suppressor gene. The sequence is then compared with known sequences of normal (wild-type or polymorphic) or mutant forms of the gene. This final step gives a result which unambiguously indicates not only whether a mutation is present, but the nature of the mutation as well.

FIG. 2 shows a cost evaluation comparing the cost of a four-level hierarchical system of the type shown in FIG. 1 compared to the cost of using sequence based diagnosis on all individuals. As can be seen, the potential savings using the method of the invention are substantial.

Having explained an example of a possible hierarchical system according to the invention, several features of the methodology will be further explained.

Features of the Diagnostic Assays Employed in the Hierarchical System

Immunoassays—Immunoassays for the VHL gene product are not currently known. However, immunoassay is included in the above hierarchical systematic assay because the procedures for raising antibodies against specific gene products are well described in the literature, for example in U.S. Pat. Nos. 4,172,124 and 4,474,893 which are incorporated herein by reference. Antibodies are normally raised which bind to portions of the gene product away from common mutation sites such that the same antibody binds to both mutant and normal protein. Preferred antibodies for use in this invention are monoclonal antibodies because of their improved predictability and specificity. It will be appreciated, however, that essentially any antibody which possesses the desired high level of specificity can be used, and that optimization to achieve high sensitivity is not required.

The antibody raised against the defective gene product is added to a portion of the patient sample under conditions where an immunological reaction will occur if the defective gene product is present, and the sample is then evaluated to see if such a reaction has occurred. The specific method for carrying out this evaluation is not critical. Examples of suitable methods include enzyme-linked immunosorbant assays (ELISA), described in U.S. Pat. No. 4,016,043, which is incorporated herein by reference; fluorescent enzyme immunoassay (FEIA or ELFA), which is similar to ELISA, except that a fluoregenic enzyme substrate such as 4-methylumbelliferyl-beta-galactoside is used instead of a chromogenic substrate, and radioinmunoassay (RIA).

From the evaluation of the first assay, the next step to be performed in the process is determined. The first assay will be either positive or negative.

If the result is positive, the high specificity of the test allows the generation of a report, either in the form of a printed report or an electronic communication, for example transmitted by electronic mail or facsimile. The report may also be in the form of an entry into a computerized patient record, which can be retrieved later by the patient's physician.

If the result of the immunoassay is negative, the possibility of a false negative test precludes reaching any firm conclusion on the existence of a mutation. In this case, the sample is retested using the next test in the hierarchical system.

Probe-Based Tests—Where there are recognized sites of likely point mutations, a suitable second test is a nucleic acid probe-based test. Probe-based tests in accordance with the invention can be any of several general types. For example, suitable probes for hybridization assays overlap with the known "hot-spot" mutation sites. When probing for mutations, as in standard dot-blot hybridization procedures, probes are synthesized to be complementary to either the normal nucleic acid sequence or to recognized mutations. The presence or absence of hybridization indicates whether the target DNA corresponds to the test probe. As epidemiological data accumulates, it will be possible to identify hot-spot sites to further reduce the number of probes that need to be applied to obtain a diagnosis.

Another type of probe-based test makes use of amplification primers which flank the site of a possible mutation. DNA is then amplified using the polymerase chain reaction (described below) and combined with a labeled oligonucleotide probe which binds specifically to a portion of the amplified DNA spanning the possible mutation site in either its mutant or wild-type form. The presence or absence of hybridization is detected, and indicates the presence or absence of a mutation.

Numerous variations on this basic method are known and can be used in the practice of the present invention. For example, the amplified DNA may be made by using primers wherein one member of the primer pair is biotinylated. In this case, the strand made using the biotinylated primer is easily isolated by binding it to avidin or streptavidin beads, and denaturing and washing off the complementary strand. The single strand may then be probed with an ASO. Alternatively, a panel of probes specific for various known mutations can be immobilized as an array on an avidin or streptavidin support and then probed with patient DNA.

A further type of test is one which does not require PCR amplification. In these tests, a probe specific for a DNA sequence is made with an RNA linker flanked by DNA. One end of the probe is labeled. The probe is mixed with the target DNA at the temperature which allows the full length probe to hybridize to the target. In the mix is the enzyme RNase H, which specifically cleaves RNA in RNA:DNA hybrids, but not single stranded RNA. As the temperature is lowered, the enzyme becomes active and if the probe has found a target it will be cleaved by the enzyme. The temperature is then raised and the any cleaved probe (which is now shorter) will melt off the target, opening up a space for more full length probe to bind. This process is repeated to build up a sufficient amount of cleaved probe to be detectable by gel electrophoresis.

Amplification Reactions—Prior to the testing of a sample using the direct hybridization method described above, the nucleic acids in the sample may be selectively amplified using a technique such as Polymerase Chain Reaction (PCR) amplification. This technique, which is described in U.S. Pat. Nos. 4,683,202 and 4,683,195, which are incorporated herein by reference, makes uses of two amplification primers each of which hybridizes to a different one of the two strands of the DNA duplex at a region away from the site of the mutation being tested for. Preferably, the primers will hybridize with non-coding portions of the DNA sequence (introns) located adjacent to the coding portion of the DNA sequence (exon) and splice-site junction containing the possible mutation site. Multiple cycles of primer extension, and denaturation are used to produce additional copies of DNA to which the primers can hybridize. In this way, the number of copies of the gene or exon of interest can be increased, thereby increasing both the specificity and the sensitivity of the method.

PCR can also be used as part of a molecular weight probe assay to detect insertion or deletion mutations. In this procedure, the DNA in a sample is amplified using a defined pair of primers for each exon of the VHL tumor suppressor gene, and the amplified product is analyzed using electrophoresis. If the primers are selected to bind to introns adjacent to an exon of interest, the presence of insertion or deletion mutations can be determined by evaluating the molecular weight of the amplified portion of the gene. This procedure can advantageously be used in a "multiplexed" format, in which primers for a plurality of exons (generally from 2 to 8) are co-amplified, and evaluated simultaneously on a single gel. This is made possible by careful selection of the primers for each exon. The amplified fragments spanning each exon are designed to be of different sizes and therefore distinguishable on an electrophoresis/size separation gel. The use of this technique has the advantage of detecting both normal and mutant alleles in heterozygous individuals. Furthermore, through the use of multiplexing it can be very cost effective.

One of the challenging steps in designing a cost effective hierarchical system of tests for diagnosis of VHL tumor suppressor gene mutation is the selection of oligonucleotide primers for use in amplification reactions. While considerable variation is possible in the sequence of the primers used in amplifying the exons, these primers are preferably optimized for use in the present invention.

Looking first at the primers used, it will be understood that in order to avoid the possibility of false positive results the primer pair, i.e., the combination of the 5'-primer and the 3'-primer for any given exon must be unique to the VHL tumor suppressor gene so that only the VHL tumor suppressor gene will be amplified. This means that the primer sequences will be generally somewhat longer than the minimum which can be used as an amplification primer. Preferred primers are from 18 to 23 nucleotides in length, without internal homology or primer—primer homology. It is also desirable for the primers to form more stable duplexes with the target DNA at the primer's 5'-ends than at their 3'-ends, because this leads to less false priming. Stability can be approximated by GC content, since GC base pairs are more stable than AT pairs, or by nearest neighbor thermodynamic parameters. Breslauer et al., "Predicting DNA duplex stability from base sequence", Proc. Nat'l Acad. Sci. USA 83: 3746–3750 (1986). In addition, to ensure complete amplification of each exon, the two primers of a pair are preferably selected to hybridize in the introns immediately flanking the exon to be amplified using the primer pair.

Additional factors apply to the selection of primers for multiplexed amplification of exons. These factors are discussed in Rylchik, W., Selection of Primers for Polymerase Chain Reaction", in Methods in Molecular Biology, Vol. 15: PCR Protocols: Current Methods and Applications, White, B. A. ed., Humana Press, Totowa, N.J., 1993. Briefly, applying these factors, primer pairs are selected by position, similarity of melting temperature, internal stability, absence of internal homology or homology to each other, i.e., they won't stick to each other or to themselves, and the 3'-end will not form a stable hairpin loop back on itself.

Thus, in the present case, the goal is to have sets of primer pairs with approximately the same thermal profile, so that they can be effectively co-amplified together. This goal can be achieved by having groups of primer pairs with approximately the same length and the same G/C content. In addition, it is preferred that the length of the gene region between the primer binding sites on a normal VHL tumor suppressor gene differ for each exon to be multiplexed as a group. Differences of only one base in length are sufficient, provided a high resolution gel capable of resolving one base differences is used in analyzing the amplification products. However, greater differences in length are preferred.

To evaluate compatibility of primers for use in co-amplification, it is desirable to determine the predicted melting temperature for each primer. This can be accomplished in several ways. For example, the melting temperature, Tm, can be calculated using either of the following equations:

$$Tm(° C.) = 81.5 + 16.6 \times \log[Na] + 0.41 \times (\%GC) - 675/\text{length}$$

where [Na] is the concentration of sodium ions, and the %GC is in number percent, or $$Tm(° C.) = 2(A+T) + 4(G+C)$$

where A, T, G, and C represent the number of adenosine, thymidine, guanosine and cytosine residues, respectively in the primer. In general, primers for co-amplification should be selected to have predicted melting temperatures differing by less than 4° C.

Several alternative techniques for diagnosing mutations may be part of the hierarchical system. For example, PCR primers which bind specifically to mutated exons can be employed in the amplification to detect either key point mutations as well as insertion and deletion mutations. In this case, product will only be observed in the electrophoresis gel if hybridization of the primer occurred. Thus, the appearance of amplification product is an indicator of the presence of the mutation, while the length of the amplification product may indicate the presence of additional mutations.

PCR amplified exon-containing fragments can also be assessed using an enzyme such as Cleavase (Third Wave Technologies, Madison, Wis.). Cleavase digests single stranded DNA at sites in the molecule apparently determined by the secondary structure adopted by the molecule. Since the secondary structure is heavily influenced by the nucleotide sequence of the molecule, point mutations and insertion/deletion mutations result in different conformations, which are digested differently by Cleavase. VHL tumor suppressor mutations may be identified by differences from expected observations in Cleavase digests.

Another means for identifying mutations in PCR amplified exon-containing fragments is in a SLAM™ assay, as disclosed in U.S. patent application Ser. No. 60/003,038, now abandoned and incorporated herein by reference. In this type of assay, short oligonucleotides complementary to and sequentially aligned with one of the amplified strands of a wild-type gene are added to the fragment mixture along with an appropriate buffer. The 5 prime end of the most 5 prime molecule is labelled with a detectable label. A thermal-stable ligase is added to the mixture and the mixture is repeatedly heated and cooled for 15–40 cycles. If no mutation is present all the oligonucleotides will successfully hybridize to the amplified strand, and full length ligation products will result. Where, however, a mutation is present, the oligonucleotide which fails to hybridize well due to the mutation will not be ligated successfully. Ligation products will be shorter. And, not only will the results show the presence of the mutation, but the approximate location of the mutation is also revealed.

Indirect Reactions—Evaluation of gene products by immunoassay and nucleic acid hybridization probe-based assays, such as fragment analysis, are properly considered "indirect" methods, because the presence or absence of a mutation is inferred from the interaction of the sample with a test reagent. Other indirect methods of testing for may also be employed in the method of the invention as one test in the hierarchical system of test methods, either in place of in addition to immunoassay or probe-based methods. For example, Single-Stranded Conformational Polymorphism (SSCP) which relies on the shape of the folded gene, Restriction Fragment-Length Polymorphism (RFLP) which relies on the length of specific DNA fragments produced using restriction endonucleases, or heteroduplex DNA detection can be utilized in circumstances where they offer the requisite level of specificity. Such methods are described in U.S. Pat. Nos. 4,582,788, 4,683,194, and 5,227,292, which are incorporated herein by reference.

DNA Sequencing—The final test in the hierarchical system of the invention should be a test which provides both high specificity and high sensitivity. A suitable test for this purpose is the determination of the DNA sequence of the exons and introns adjacent to these exons. This method is a direct method of DNA sequence analysis, and is generally the most costly. The general methodology employed involves amplifying (for example with PCR) the DNA fragments of interest; combining the amplified DNA with a sequencing primer which may be the same as or different from the amplification primers; extending the sequencing primer in the presence of normal nucleotide (A, C, G, and T) and a chain-terminating nucleotide, such as a dideoxynucleotide, which prevents further extension of the primer once incorporated; and analyzing the product for the length of the extended fragments obtained.

While such methods, which are based on the original dideoxysequencing method disclosed by Sanger et al., (Proc. Natl. Acad. Sci. USA 74: 5463–5467 (1977)) are useful in the present invention, the final assay is not limited to such methods. For example, other methods for determining the sequence of the gene of interest, or a portion thereof, may also be employed. Alternative methods include Maxam and Gilbert chemical sequencing (Proc. Natl. Acad. Sci. USA, 74: 560–564 (1977)) and variations of the dideoxy method and methods which do not rely on chain-terminating nucleotides at all such as that disclosed in U.S. Pat. No. 4,971,903, which is incorporated herein by reference.

Throughout this specification reference has been made to analysis of length and quantity of nucleic acid fragments and to nucleic acid sequencing. Such analysis may be done by electrophoresis, for example on a polyacrylamide gel. Automated systems designed for laboratory application are among the most convenient methods for performing such analysis. Several automated DNA sequencing apparatuses are commercially available. Methods and apparatus for sequencing of DNA are described in U.S. Pat. Nos. 4,811,218; 4,823,007; 4,881,812; 5,062,942; 5,091,652; 5,108,179; 5,119,316; 5,122,345; 5,162,654; 5,171,534; 5,190,632; 5,207,880; 5,213,673; 5,230,781; 5,242,567; 5,290,419; 5,294,323; 5,307,148; 5,314,602; 5,324,401; and 5,360,523 which are incorporated herein by reference. High speed electrophoresis under high density electric fields is described in U.S. patent applications Ser. No. 08/332,577 now U.S. Pat. No. 5,672,022; Ser. No. 08/353,932 U.S. Pat. No. 5,710,628; Ser. No. 08/332,892 U.S. Pat. No. 5,507,934; Ser. No. 08/387272 U.S. Pat. No. 5,543,018 all of which are assigned to an assignee of the instant patent application.

In the foregoing direct and indirect test formats, the type of detectable label on the reaction product of interest varies with the test itself. For example, the type of label employed on amplification primers depends on the instrument used to analyze the products of the reaction. In the case of radio-labeled primers, the analysis might be by autoradiography. The preferred labels, however, for use with many automated electrophoresis systems are fluorophores which are detected using photodiodes, photomultipliers or other light sensitive devices. For these types of devices the label must be detectable by these detectors. In other cases the choice of label is not critical. Suitable labels may include fluorophores, chemiluminescent labels, radiolabels, chemical couplers such as biotin which can be detected with streptavidin-linked enzymes, and for immunoassays, epitope tags such as digoxigenin detected using antibodies available from Boehringer-Mannheim. A preferred example of a fluorescent label is fluorescein, which is a standard label used in nucleic acid sequencing systems using laser light as a detection system.

Preferred automated electrophoresis systems will have a resolution of one base pair, so that one base deletions or insertions, which are relatively common, can be identified. A suitable gel is a polyacrylamide gel of the type recommended for use with the Pharmacia A.L.F™ Sequencer.

Optimal Diagnostic Algorithm

While the foregoing approach which requires the selection of high specificity tests such that a positive result can be treated as diagnostic works to provide a high confidence, low cost diagnostic algorithm, it is only applicable to the circumstance where high specificity tests are readily available. To further reduce the cost and yet maintain confidence in the diagnosis, a more robust approach to the selection of a diagnostic algorithm is required.

For generalized selection of an optimal or near optimal diagnostic algorithm, the first step in the process is the identification of a group of tests which might be used in the testing procedure and the calibration of these tests to identify the levels of false positives and false negatives associated with each test.

Calibration is determined on the basis of a "gold standard" test. This test is by definition 100% specific and 100% sensitive, with no false positives and no false negatives. In the field of molecular biology the closest we come to a gold standard is complete DNA sequencing. While certain errors can be anticipated, we can assume for the purposes of identifying genetic mutations that complete DNA sequencing is at least theoretically 100% accurate.

The method of calibration is as follows. A statistically meaningful number of patient samples (i.e., n>1000) is obtained from a hospital. These samples may be fresh or frozen, depending on the requirements of the test to be calibrated. Part of each sample is prepared as required by the test. For example, certain antibody tests require fresh tissue treated with certain detergents and other separating agents. The tissue sample is then subjected to the antibody test. A result is obtained: either positive for the tested antigen, or negative. After testing the patient samples, overall totals of positive and negative results are tallied.

The next step in calibration is to re-test all the patient samples with the gold standard. DNA is prepared from each of the patient samples and it is examined for mutations by sequencing. A result is obtained for each sample, and again, all the results are tallied.

Ultimately, the two sets of results are compared and four characteristics of the test are established:

(1) the sensitivity of the test, $\eta$, which is the probability that an individual with the genetic mutation of interest is correctly identified by the test; and (2) the specificity of the test, $\theta$, which is the probability that an individual lacking the genetic mutation of interest is correctly identified by the test.

With these calibration values in hand, one next evaluates various combinations of tests and test results and the costs associated with each test to find the combination of tests which gives sufficiently high performance at the lowest possible cost. This process can be exemplified using the group of tests shown in Table 1 for a genetic mutation with a prevalence, P of 0.5.

TABLE 1

| Test # | Type | n | θ | Cost |
|---|---|---|---|---|
| 1 | immunoassay | .8 | .9 | 1 |
| 2 | Fragment Analysis, | .85 | .9 | 10 |
| 3 | Partial Seguencing | 1 | .75 | 150 |
| 4 | Full Sequencing | 1 | 1 | 200 |

To define and evaluate a matrix, several parameters must be pre-defined. These are (1) the maximum number of tests which will be performed on any sample, and (2) the minimum requirements for overall sensitivity, $\eta_A$, overall specificity, $\theta_A$, overall predictive value of a positive algorithm result, $PVP_A$, which is given by the equation $$PVP_n = \frac{\pi \eta_\Pi}{\pi \eta_\Pi + (1 - \pi) Pr(T = + \mid G = -)}$$

where P is the prevalence of the genetic condition "G" being tested for in the population and Pr(A=-|G=+) is the probability that the algorithm A will yield a positive result for condition "G" when the sample is in fact negative; and overall predictive value of a negative algorithm result, $PVN_A$, which is given by the equation $$PVN_\Pi = \frac{(1 - \pi) \theta_\Pi}{(1 - \pi) \theta_\Pi + (\pi) Pr(T = - \mid G = +)}$$

where P is the prevalence of the genetic condition being tested for in the population and Pr(A=-|G=+) is the probability that the algorithm A will yield a negative result for condition "G" when the sample is in fact positive.

The various possible combinations of the tests are set up within an "Outcome mapping Matrix" An exemplary matrix for some of the possible combinations of the tests shown in Table 1, assuming that the maximum number of tests to be performed is 3 is shown in Table 2. This table evaluates all possible combinations of the four tests, other than those in which test 4, the most accurate and most expensive, is followed by another test, since such a test would be redundant and therefore only increase the cost, and rates the test result as being positive (+) or negative (−) by applying a "majority rule" as discussed by Lachenbruch, P. A., "Multiple Reading Procedures: The Performance of Diagnostic Tests", *Statistics in Medicine* 7: 549–57 (1988) with the exception that a test result for test 4 (equivalent to the gold standard) is taken as controlling.

TABLE 2

| TEST COMBO | +++ | ++− | +−+ | +−− | −++ | −+− | −−+ | −−− |
|---|---|---|---|---|---|---|---|---|
| 111 | + | + | + | + | − | − | − | − |
| 112 | + | + | + | − | + | − | − | − |
| 113 | + | + | + | − | + | − | + | − |
| 121 | + | + | + | − | + | − | − | − |
| 122 | + | + | + | − | + | − | − | − |
| 123 | + | + | + | − | + | − | + | − |
| 124 | + | − | + | − | + | − | + | − |
| 131 | + | + | + | − | + | − | − | − |
| 132 | + | + | + | − | + | − | − | − |
| 133 | + | + | + | − | + | − | + | − |
| 134 | + | − | + | − | + | − | + | − |
| 14 | + | + | − | − | + | + | − | − |
| 221 | + | + | + | − | + | − | − | − |
| 213 | + | + | + | − | + | − | + | − |
| 214 | + | − | + | − | + | − | + | − |
| 221 | + | + | + | − | + | − | − | − |
| 222 | + | + | + | − | + | − | − | − |
| 223 | + | + | + | − | + | − | + | − |
| 224 | + | − | + | − | + | − | + | − |
| 231 | + | + | + | − | + | − | − | − |
| 232 | + | + | + | − | + | − | − | − |
| 233 | + | + | + | − | + | − | + | − |
| 234 | + | − | + | − | + | − | + | − |
| 24 | + | + | − | − | + | + | − | − |
| 311 | + | + | + | − | + | − | − | − |
| 312 | + | + | + | − | + | − | − | − |
| 313 | + | + | + | − | + | − | + | − |
| 314 | + | − | + | − | + | − | + | − |
| 321 | + | + | + | − | + | − | − | − |
| 322 | + | + | + | − | + | − | − | − |
| 323 | + | + | + | − | + | − | + | − |
| 324 | + | − | + | − | + | − | + | − |
| 331 | + | + | + | − | + | − | − | − |
| 332 | + | + | + | − | + | − | − | − |
| 333 | + | + | + | − | + | − | + | − |
| 334 | + | − | + | − | + | − | + | − |
| 34 | + | + | − | − | + | + | − | − |

Other standards for assigning an overall test result might also be employed in this stage of the analysis, including one which gave greater weights to highly sensitive and specific tests, or one which required unanimity.

Whatever method is used for assigning the results in the Outcome Mapping Matrix, the outcomes are then used to determine values for overall sensitivity, $\eta_A$, overall specificity, $\theta_A$, $PVP_A$, and $PVN_A$. This process is best understood through the use of examples taken from Table 2.

Looking first to the row for test combination 122, there are four combinations of test results which yield a overall positive test result. The overall sensitivity, $\eta_A$, is given by the sum of a corrected sensitivity term for each such result combination. For the first result combination, +++, the corrected sensitivity term is $\eta_1 * \eta_2 * \eta_2$ or in the case of the values shown in Table 1, 0.578. For the second result combination ++−, the corrected sensitivity term is $\eta_1 * \eta_2 * (1-\eta_3)$ or 0. For the third result combination, +−+, the corrected sensitivity term is $\eta_1 * (1-\eta_2) * \eta_3$ or 0.12. Finally for the fourth result combination, −++, the corrected sensitivity term is $(1-\theta_1) * \theta_2 * \eta_3$ or 0.17. When these numbers are added together, an overall sensitivity term $\eta_A$ of 0.97 is obtained.

In similar fashion, an overall value for specificity of $\theta_A$ is determined. In this case, the negative tests are evaluated, and the values of $\theta$ for the individual tests are combined. In the case of the 122 test in Table 2, this yields an overall specificity of 0.972.

Using this same technique, the remaining values for $\eta_A$ and $\theta_A$ can be determined in the same manner. Values for a few algorithms are shown in Table 3. These values can then be used to determine $PVP_A$ and $PVN_A$ using the formulas given above for those combinations where $\eta_A$ and $\theta_A$ are within the threshold criteria. The term $Pr(A=+|G=-)$ in the absence of ambiguous outcomes in the outcome mapping matrix is $(1-\theta_A)$. If the outcome mapping matrix contains ambiguous results (for example if an even number of tests is evaluated using a majority rule), the result combinations which yield positive tests results in the outcome mapping matrix are assumed to be false positives, and the probability of such a false positive is determined by taking multiplying the value of $(1-\theta)$ for positive results within the combination, and $\theta$ for negative results within the combination. Conversely, $Pr(A=-|G=+)$ is given by $(1-\eta_A)$ in the absence of ambiguous results.

TABLE 3

| ALGORITHM | $n_A$ | $\theta_A$ | PVPA | PVNA |
|---|---|---|---|---|
| 111 | .896 | .972 | .969 | .903 |
| 112 | .912 | .972 | .970 | .917 |
| 121 | .912 | .972 | .970 | .917 |
| 122 | .926 | .972 | .971 | .929 |
| 211 | .927 | .972 | .971 | .930 |

If all of the algorithms are being considered, a threshold for acceptable performance, i.e., $\eta_A{}^3$ 0.95, $\theta_A{}^3$ 0.95, $PVP_A{}^3$ 0.99 and $PVN_A{}^3$ 0.99 may be applied to eliminate some of the algorithms from further consideration. For the remainder, the expected cost of performing the tests defined by the algorithm is determined.

The expected cost of performing the test, $E[C_A]$ is given by the equation $$E(C_A) = \sum_{r=1}^{n}\left(p_{A,r}\sum_{j=1}^{r}C_{(j)}\right)$$

where $P_{A,r}$ is the probability that a given number of tests (r) will have to be performed to achieve an unambiguous answer, $C_{(j)}$ is the cost of each test j in the algorithm, and the summation from j=1 to r is the sum of the cost for the first r tests in the algorithm. To understand this calculation, one can again look at test 122. In the case where the first two tests are either both positive or both negative, the outcome mapping matrix is controlled by these tests and the third test does not have to be performed. In an individual carrying the mutation of interest, the probability of getting positive tests for tests 1 and 2 is given by $\eta_1*\eta_2$ or 0.68, while the probability of getting two negative test results is given by $(1-\eta_1)*(1-\eta_2)$ or 0.03. In a mutation free individual, the probability of getting positive tests for tests 1 and 2 is given by $(1-\theta_1)*(1-\theta_2)$ or 0.01, while the probability of getting two negative test results is given by $\theta_1*\theta_2$ or 0.81. $P_{A,2}$, the probability that these two tests will be enough, is then equal to (0.68+0.03)P+(0.01+0.81)(1-P) or 0.765. The probability that all three tests will have to be done is 1-0.765 or 0.235. Applying these numbers to the costs of tests 1 and 2 (11) and tests 1, 2 and 2 (21), the total cost of the test is 13.35.

Applying this type of calculation to the selected algorithms of Table 3, the costs shown in Table 4 result.

TABLE 4

| ALGORITHM | EXPECTED COST |
|---|---|
| 111 | 2.25 |
| 112 | 4.50 |
| 121 | 11.23 |
| 122 | 13.35 |
| 211 | 11.23 |

It will be understood that the example utilized above which involves only four possible tests, is in fact a simple example, and that normal analysis may involve many more combinations of tests, or that larger or smaller numbers of tests may be permitted in the analysis. In addition, in deterimining the optimal algorithm, an evaluation of cost resulting from performing varying numbers of tests, i.e, 2 tests, 3 tests, 4 tests etc. may be useful in identifying the algorithm which actually provides the greatest economic advantage. Further, it will be understood that reassessment of the optimum test combination would be advantageously performed whenever new tests for a disease-associated mutation become available, or even in response to significant cost changes for previously evaluated tests. These tests can be readily evaluated out using the outline set forth above.

Intron Sequences

Before turning to the preferred hierarchical system for diagnosis of VHL tumor suppressor disease-associated mutations, the VHL tumor suppressor gene intron sequences towards which the present invention is also directed will be disclosed. These sequences have been obtained by sequencing genomic DNA. As indicated in FIG. 3, these sequences, set out below as SEQ ID NO:1 through SEQ ID NO:5, lie in human chromosome 3 adjacent to the exons of the VHL gene which are found in the VHL cDNA (CenBank Accession No. L15409):

[SEQ ID NO:1]

Location: 5' leader/contiguous to 5' end of disclosed cDNA.

```
1    gaattcagtt agttgacttt ttgtacttta taagcgtgat gattgggtgt tcccgtgtga 61   gatgcgccac cctcgaacct tgttacgacg tcggcacatt gcgcgtctga catgaagaaa 121  aaaaaaattc agttagtcca ccaggcacag tggctaaggc ctgtaatccc tgcactttga 181  gaggccaagg caggaggatc acttgaaccc aggagttcga gaccagccta ggcaacatag 241  cgagactccg tttcaaacaa caaataaaaa taattagtcg ggcatggtgg tgcgcgccta
```

```
301 cagtaccaac tactcgggag gctgaggcga gacgatcgct tgagccaggg aggtcaaggc 361 tgcagtgagc caagctcgcg ccactgcact ccagcccggg cgacagagtg agaccctgtc 421 tccaaaaaaa aaaaaaaaca ccaaaccttta gagggtgaa aaaaaatttt atagtggaaa 481 tacagtaacg agttggccta g
```

[SEQ ID NO:2]

Location: First Intron 5' end/ contiguous to 3' end of exon 1

```
1   (AG)gtacggg cccggcgctt aggcccgacc cagcaggacg atagcacggt ctaagcccct 58  ctaccgcccc ggggtccatt cagacgggga actaggcccc ttgaggcagg acacatccag 118 ggt
```

[SEQ ID NO:3]

Location: First Intron 3' end/ contiguous to 5' end of exon 2

```
1   ctcctgacct ctatgatccg cctgcctcgg cctccaaagt gctgggatta caggtgtggg 61  ccaccgtgcc cagccaccgg tgtgggctct ttaacaacct ttgcttgtcc cgatag (GT)
```

[SEQ ID NO:4]

Location: Second Intron 5' end/ contiguous to 3' end of exon 2

```
1   (AG) g tactgacgtt ttacttttta aaaagataag gttgttgtgg taagtacagg 52  atagaccact tgaaaaatta agcccagttc tcaattttttg cctgatgtca ggcacggtat 112 ccaatctttt tgtatcctat tctctaccat aaataaaatg gaagtgatga tttt
```

[SEQ ID NO:5]

Location: Second Intron 3' end/ contiguous to 5' end of exon 3]

```
1   ctacagaagg catgaacacc atgaagtgtc catagggggcc acagcataca cactgccaca 61  tacatgcact cacttttttt ctttaaccta aaagtgaaga tccatcagta gtacaggtag 121 ttgttggcaa aagcctcttg ttcgttcctt gtactgagac cctagtctgc cactgaggat 181 ttggtttttg ccccctagtc tgccactgag gatttggttt ttgcccgttc cag (TG)
```

The abbreviations used for the nucleotides are standard in the art.

In FIG. 3 the location of the introns are indicated relative to the VHL tumor suppressor gene cDNA disclosed in the GenBank accession No. L15409. Intron 1 falls between nucleotides 553 and 554 of the disclosed cDNA while intron 2 falls between nucleotides 676 and 677 of the disclosed cDNA. It is noted that the full intron sequences are not disclosed as they are not yet determined.

With one exception, these intron sequences do not encode a known polypeptide, and are presumably edited by splicing in the construction of the mature mRNA. The one exception occurs in the 159 nt of 5' leader sequence immediately upstream of the ATG initiation codon in the mature mRNA. This sequence happens to encode an open reading frame which may be an artifact, or it may represent an alternative form of the mRNA, which has an alternative promoter further upstream from the one used to initiate the cDNA identified in the GenBank accession No. L15409.

Intron regions in general tend to show a degree of variability not found in exon regions, and it is contemplated that variations may be found among the general population. It should be noted that the DNA sequence set forth above represents a preferred embodiment of the present invention. However, variations of sequence exist which are functionally equivalent to the sequence set forth above and which are associated with VHL disease. Such DNA sequences which are functionally equivalent to the sequence set forth above and which appear as introns of the VHL tumor suppressor gene are intended to be encompassed within the present invention.

This invention also encompasses oligonucleotide fragments of the intron sequences noted above. These oligonucleotides, which may be used among other things as probes or primers, are anticipated to be at a minimum 12 nucleotides in length, and they may extend up to the full length of the above disclosed sequence (or even longer if they include exon sequences or other additional sequences). Preferred oligonucleotide fragments for sequencing and amplification reactions have lengths of from 18 to 24 nucleotides. They can be derived from any part of the intron, but reaction kinetics driven by factors such as G:C content and secondary structure will affect the usability of some fragments.

Further, this invention also encompasses the complements to the intron sequences noted above. Complements are polynucleotides with sequences that form the second, matching, strand of a DNA helix. The sequence of a complementary strand consists of nucleotides which match the first strand in normal base pairing (i.e. A:T and C:G pairing) but in the opposite 5' to 3' orientation. Complements are important in part because amplification and sequencing primers may be designed to hybridize with the complementary strand. Fragments of complements greater than 12 nucleotides in length are therefore included in the invention.

This invention encompasses the above noted polynucleotides in their purified forms. For the purposes of this specification and the claims herein "purified" refers to functional purity, where purity is sufficient for the polynucleotide to function as required by the assays employed.

Preferred Hierarchical System for Diagnosis of VHL Tumor Suppressor Disease-Associated Mutations To further exemplify the method of the invention, FIG. 4 shows a preferred hierarchical system suitable for diagnosis and targeted screening for mutations in the VHL tumor suppressor gene.

Figure 5:
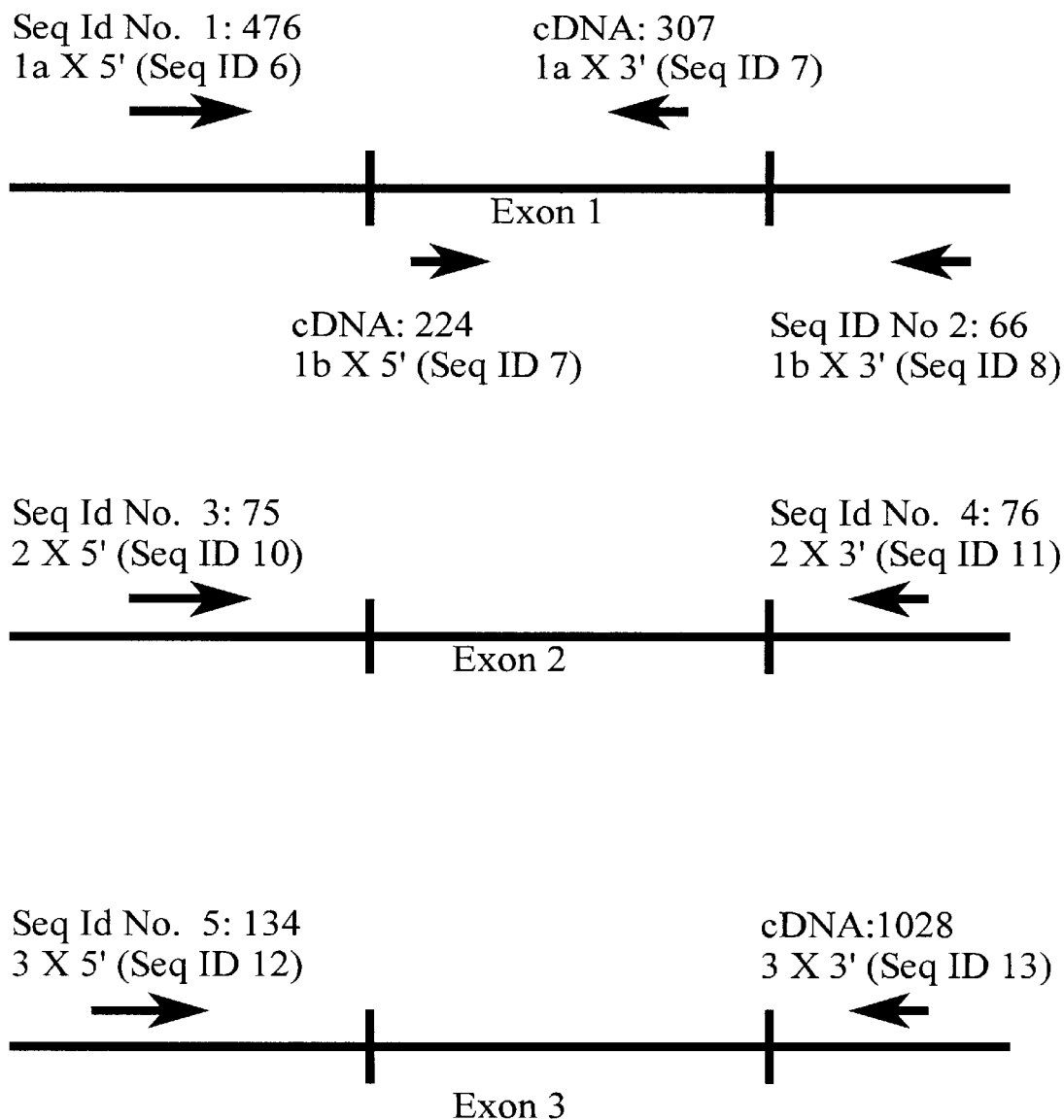
FIG. 5 identifies the location of preferred amplification primers for diagnosis of VHL tumor suppressor mutations.

The first step in the hierarchical system is a multiplexed fragment analysis test. As described above, this test is used for detection of insertion/deletion mutations and for copy number mutations. To successfully amplify the fragments by PCR, the following strategy is employed. Exon 2 is conveniently amplified from its flanking intron sequences, as is Exon 3. Because of its large size, Exon 1 is conveniently amplified in two separate reactions, 1a and 1b. In this case, one of the primer pairs hybridizes to an intron region, while the other primer hybridizes within the exon. The locations of the primers used are identified in FIG. 5. The sequences of the amplification primers employed and the expected length of fragments are [SEQ ID NO:6 through SEQ ID NO:13]:

profiles. Exon 1b is preferably amplified by itself; Exon 3 is also preferably amplified by itself.

It is useful to employ a control fragment amplification in each reaction. Control fragments are usefully taken from a different chromosome in a highly conserved region of DNA which is not known to be likely to mutate or increase copy number, and is not resistant to amplification. Such a control allows the investigator to determine the success of the amplification reaction. As well, it allows comparison between samples because the amount of amplification of the control sequence can be taken as a normalized amount for comparison of copy number mutations. Further, a control sequence also gives a fragment size which can be used as a basis to determine other fragment sizes.

Quantitative analysis of copy number mutation can be achieved if the amplification reaction is carried out for a limited number of amplification cycles. It will be understood, that the more cycles of amplification are carried out, the more of the desired product will be made and thus the easier its detection will be. It should also be recognized, however, that during the initial cycles (generally the first 20–25 cycles), the amount of DNA of the desired sequence doubles in each cycle, while thereafter the yield of desired product drops off. For maximum effectiveness in the method of the present invention, the amplification of the exons in the patient sample should be carried out only for a number of cycles during which doubling of DNA is still being achieved. Such amplification is referred to in the specification and claims hereof as "quantitative" amplification.

|  | Amplification Primers | Expected Length of Fragment |
|---|---|---|
| Exon 1a × 5' | GGA AAT ACA GTA ACG AGT TGG CCT [SEQ ID NO:6] | 328 nt |
| Exon 1a × 3' | CCT CCC CGC CGT CTT CTT CA [SEQ ID NO:7] |  |
| Exon 1b × 5' | GGG CGG AGA ACT GGG ACG AG [SEQ ID NO:8] | 396 nt |
| Exon 1b × 3' | GGG CGG TAG AGG GGC TTA GA [SEQ ID NO:9] |  |
| Exon 2 × 5' | CAC CGG TGT GGG CTC TTT A [SEQ ID NO:10] | 241 nt |
| Exon 2 × 3' | GGG CTT AAT TTT TCA AGT GGT C [SEQ ID NO:11] |  |
| Exon 3 × 5' | CCTCTTGTTCGTTCCTTGTA [SEQ ID NO:12] | 471 nt |
| Exon 3 × 3' | TTTGTGATGTTTGCCCCTAA [SEQ ID NO:13] |  |

Amplification primers can be taken from any part of the intron sequences disclosed in the instant application, or from the cDNA sequence listed at GenBank Accession No. L15409. Indeed the primers may be selected from genomic DNA regions outside of the currently known sequences, and it is anticipated that such sequences shall eventually become known. However, the now known sequences are most useful, because fragments amplified from them will likely contain all the mutations of clinical significance, and they are short enough to be easily manipulated on an electrophoresis analysis gel. That being said, the selection of the above primers is only an example of convenient primer pairs that are found to be superior. A worker skilled in the art will be able to select other primers which are useable for amplifications. The test for selecting a primer is whether the primer results in amplification of the exon containing fragment.

It is found that amplifications for exons 1a and 2 may be conveniently multiplexed, as they share thermal cycling Quantitative amplification is particularly important as a diagnostic tool since Loss of Heterozygosity (LOH) is found in nearly 90% of clear cell renal carcinomas. (Gnarra et al, supra).

Having performed the quantitative amplifications as described above, the individual patient samples are examined in an automated DNA sequencer apparatus for insertion and deletion mutations, and for copy number mutations. For patients wherein disease-causing mutations are identified, patient reports are prepared. For patients where no diagnosis is obtained, their body samples are re-examined using the next level of the hierarchical system.

Figure 6:
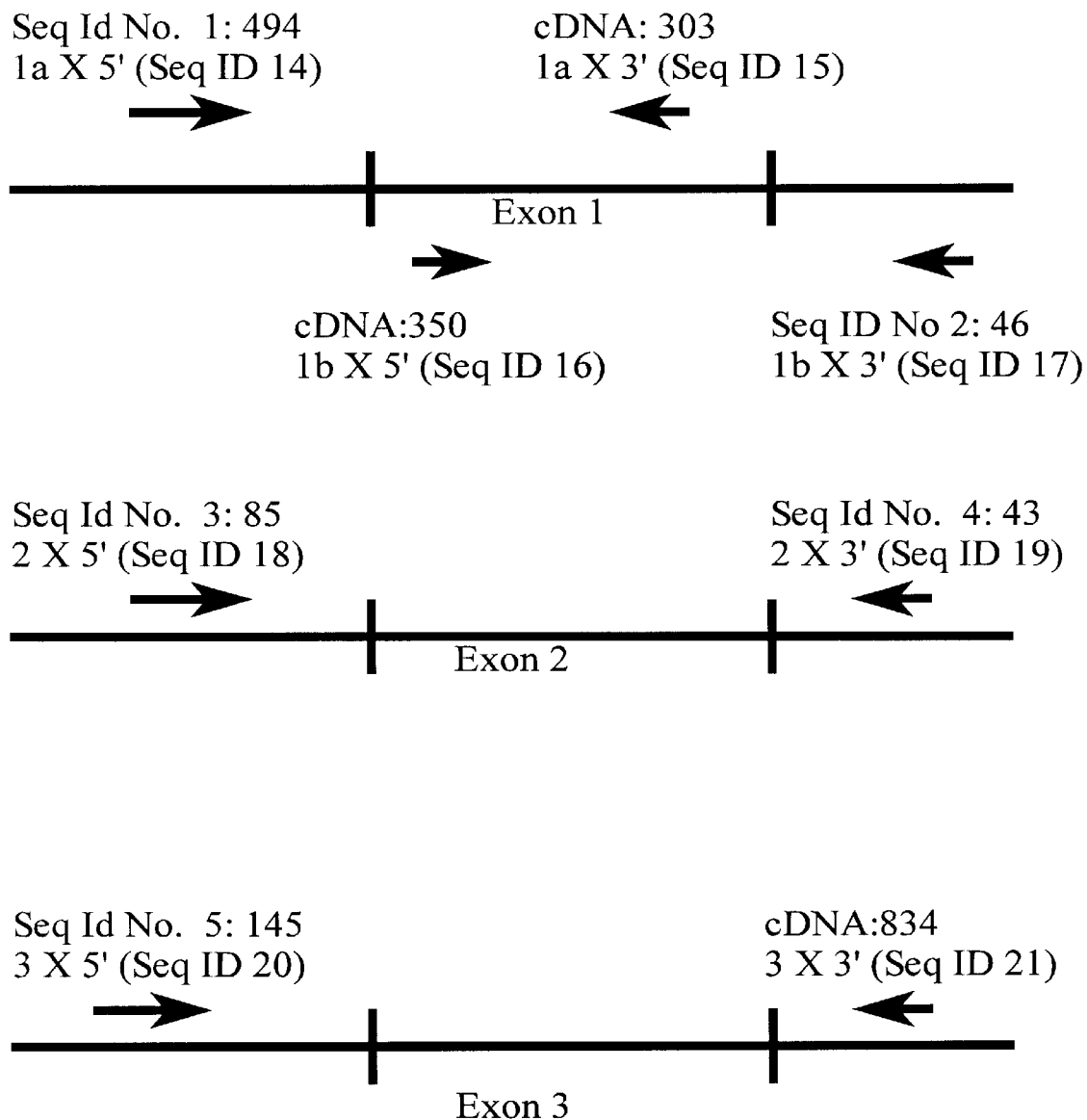
FIG. 6 illustrates the location of primers found to be suitable for DNA sequencing, according to the method described for selecting primers hereinabove.

As illustrated in FIG. 4, the next level of the hierarchical system is DNA sequencing of at least one exon of the VHL tumor suppressor gene. Any method of DNA sequencing may be employed, but the well known Sanger dideoxy chain-termination method is among the simplest. In order to obtain DNA sequence the exon containing fragments are again amplified, this time individually. The next step is to perform sequencing using a labelled sequencing primer. The location of primers found to be suitable for DNA sequencing, according to the method described for selecting primers hereinabove, are illustrated in FIG. 6. In general, sequencing primers are nested inside the amplification primers, although the amplification primers themselves could be used for sequencing purposes if desired. The DNA sequences of these primers are SEQ ID NO: 14–21:

| Name | Sequence |
|------|----------|
| vh1-5'X1aseq | TGGCCTCGCCTCCGTTAC [SEQ.14] |
| vh1-3'X1aseq | CCCGCCGTCTTCTTCAGG [SEQ ID NO:15] |
| vh1-5'X1bseq | AAGAAGACGGCGGGGAGG [SEQ ID NO:16] |
| vh1-3'X1bseq | CCGTGCTATCGTCCTGCTG [SEQ ID NO:17] |
| vh1-5'X2seq | GGCTCTTTAACAACCTTT [SEQ ID NO:18] |
| vh1-3'X2seq | TACCACAACAACCTTATC [SEQ ID NO:19] |
| vh1-5'X3seq | TTCCTTGTACTGAGACCCTA [SEQ ID NO:20] |
| vh1-3'X3seq | TGCAATGCGCTCCTGTGTCA [SEQ ID NO:21] |

Sequencing primers can be designed for either directional orientation.

Having performed the reactions as described above for at least one exon, the individual patient samples are examined in an automated DNA sequencer for point mutations, previously unobserved insertion/deletion mutations, inversions and other possible disease-associated mutations. If no such mutation is identified, then further exons are sequenced. If a mutation is found in one of the sequences, a patient report is prepared without further testing. If no mutation is found under any of the above tests, then the VHL tumor suppressor gene corresponds to a wild-type gene and a patient report is prepared accordingly.

The amplification and sequencing primers used in the present invention are advantageously packaged as kits for the detection of mutations in the VHL tumor suppressor gene. The primers may be packaged individually within the kit, or as mixtures of primers, sometimes referred to as "primer cocktails", which are useful in a single reaction vessel. Such kits may contain a single pair of primers, useful for quantitative amplification of a single exon, or multiple pairs of primers useful for amplification of multiple exons. Such kits may further include amplification and/or sequencing primers for one or more exons. Such kits may also include reagents other than primers for use in the amplification reaction, such as a polymerase and buffers, but this is optional.

Preferred kits in accordance with the invention comprise a plurality of primer pairs useful in the co-amplification of a plurality of exons of the VHL tumor suppressor gene. Primer pairs in such kits are selected to have a common melting temperature and to produce amplification products having differing lengths.

The following non-limiting example illustrates an application of the invention.

EXAMPLE 1

In order to diagnose VHL tumor suppressor gene mutation in a plurality of patients, the following hierarchical system of tests was performed.

Level 1: DNA Fragment Length/Quantity Analysis

Quantitative fragment length and amount analysis was performed to assay for, or diagnose: 1) the presence of an insertion or deletion mutation; 2) whether the patient was homozygous or heterozygous for the insertion or deletion mutation; and 3) whether there had been a copy number mutation which has increased the ploidy of the gene.

DNA was prepared from either blood or biopsy samples from each patient using a QIAamp Kit (Qiagen Inc, Chatsworth Calif.) according to accompanying directions. Briefly, for blood samples or lymphocyte-containing fractions thereof, the sample was combined with a lysing solution containing SDS to which Proteinase K was added, mixed, and allowed to incubate, to lyse the cells. Ethanol was added and the lysate was transferred to a QIAamp spin column from which DNA was recovered after several washings. Tumor tissue can be similarly processed if it is first mulched with scissors.

To perform the fragment length and quantity analysis, the genomic DNA was amplified in three sets:
Pool A: Exons 1a, 2 and the C4 control;
Pool B: Exon 1b and C4 control; and
Pool C: Exon 3 and C4 control,
using the following multiplexing amplification primers:

| | Amplification Primers |
|---|---|
| Exon 1a × 5' | GCA AAT ACA GTA ACG AGT TGG CCT [SEQ ID NO:6] |
| Exon 1a × 3' | CCT CCC CCC CCT CTT CTT CA [SEQ ID NO:7] |
| Exon 1b × 5' | CGG CCC ACA ACT CCC ACG AG [SEQ ID NO:8) |
| Exon 1b × 3' | CCC CCC TAC ACC CCC TTA CA [SEQ ID NO:9] |
| Exon 2 × 5' | CAC CCC TCT CCC CTC TTT A [SEQ ID NO:10] |
| Exon 2 × 3' | CCC CTT AAT TTT TCA ACT CCT C [SEQ ID NO:11] |
| Exon 3 × 5' | CCTCTTCTTCCTTCCTTCTA [SEQ ID NO:12] |
| Exon 3 × 3' | TTTCTCATCTTTCCCCCTAA [SEQ ID NO:13] |
| C4X5'(control) | CTCACCCGCACCTAACTTT [SEQ ID NO:22] |
| C4X3'(control) | CCAGGATGACACCCCATCCCA [SEQ ID NO:23] |

The primers were synthesized on an Expedite™ Nucleic Acid Synthesis System (Millipore, Inc.) using reagents standard for that system. One primer of each amplification pair was labelled with the fluorescein based fluorophore, FITC, according to the manufacturer's instructions.

The members of pool A were selected because they use a hybridization temperature of 55° C. and none of the expected fragment lengths would overlap in an electrophoresis gel. The expected fragment lengths were, respectively,
exon 1a=328 nt
exon 2=241 nt
C4 (control)=282 nt Multiplexing pool B consisted of Exons 1b and the C4 control. The members of pool B were selected because they use a hybridization temperature of 55° C. and none of the expected fragment lengths would overlap in an electrophoresis gel. This pool is not combined with pool A because overlapping fragments of genomic DNA are amplified in the two separate reactions. The expected fragment lengths were, respectively,
exon 1b=396 nt
C4 (control)=282 nt Multiplexing pool C consisted of Exons 3 and the C4 control. The members of pool C were selected because they use a hybridization temperature of 52° C. and none of the expected fragment lengths would overlap in an electrophoresis gel. The expected fragment lengths were, respectively,
exon 3=471 nt
C4 (control)=282 nt Each 25 microliter multiplexed PCR reaction contained 300 ng patient sample genomic DNA, 50 ng of each primer, 200 nM dNTPs, 50% DMSO, and 2.5 units Taq polymerase in a 1× PCR buffer containing 10 mM Tris pH 8.3, 50 mM KCl, 1.5 mM MgCl$_2$ and 0.001% (w/v) gelatin. The reaction mixture was mixed well and placed in a Perkin-Elmer 9600 thermo-cycler. The reaction mixture was immediately heated to 94° C. for 2 minutes to denature all oligonucleotides. Then followed 19 temperature cycles in the following order:
55° C. (Pool A and B); 52° C. (Pool C) for 1.5 min;
65° C., 2.0 min; and
94° C., 1.0 min.

A final extension at 65° C. for 7 mins concluded the thermal cycling. The amplification was stopped by the addition of a denaturing loading buffer and cooling to room temperature. The denaturing loading buffer consisted of an equal volume of 100% formamide with 5 mg/ml dextran blue.

The reaction products were then loaded into a polyacrylamide gel for electrophoretic separation. Electrophoretic separation took place in a semi-automated electrophoresis apparatus, the Pharmacia A.L.F™ Automated DNA Sequencer, controlled by HELIOS™ operating software. The electrophoresis gel construction, pre-run, sample run, and all other aspects of the process were performed according to the manufacturer's instructions.

Figure 7A:
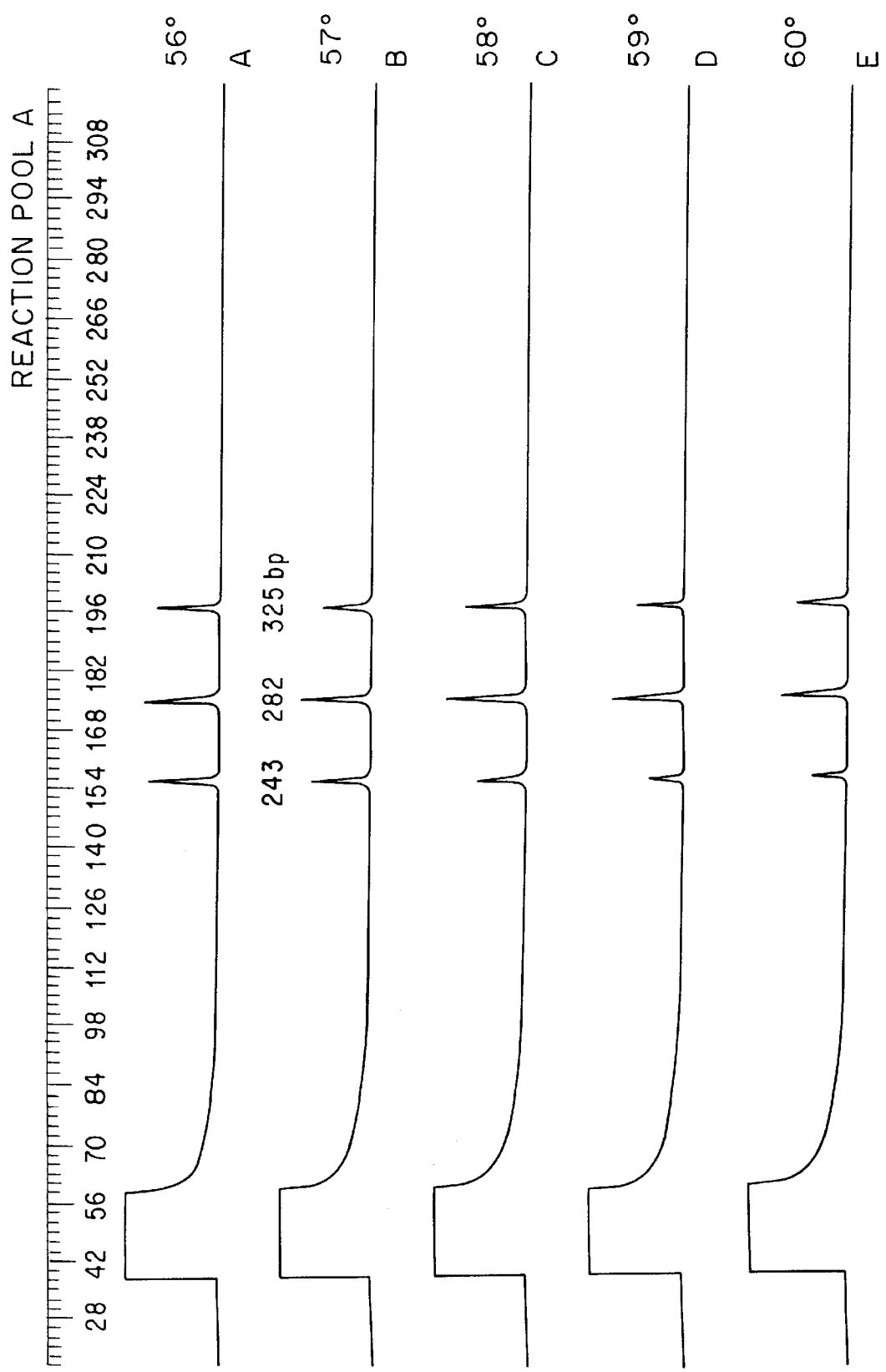
FIG. 7 (FIGS. 7(a), 7(b) and 7(c)) illustrates the standard values for the amplified exons obtained from multiplexing pools A, B and C.
Figure 7B:
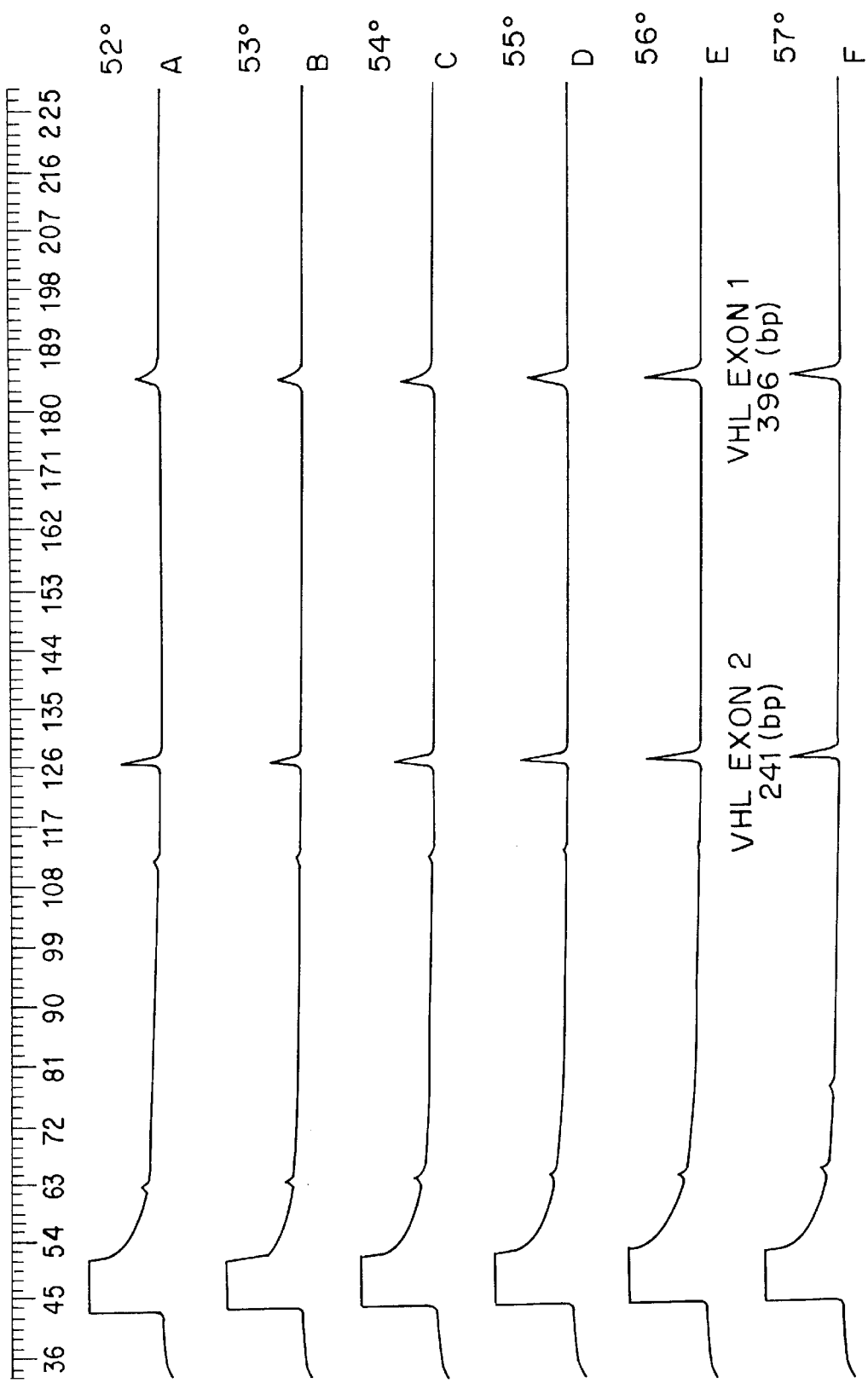
Figure 7C:
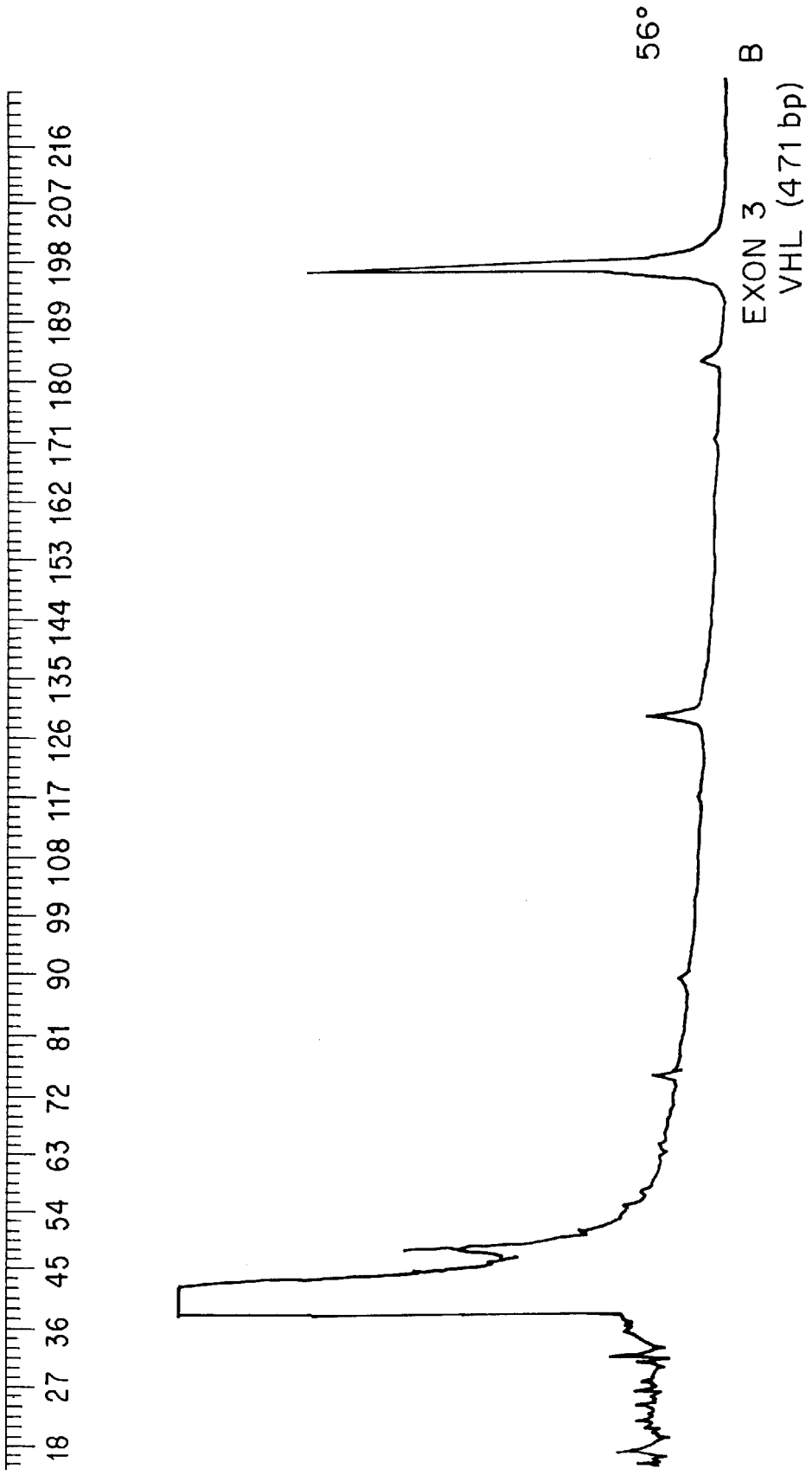

The amplified fragments detected on the A.L.F.™ were analyzed for length and were compared to the expected sizes of the normal gene fragments. FIG. 7 illustrates the standard values for the amplified exons obtained from multiplexing pools A, B and C. A stepwise comparison of the fragments from the patient sample reactions and the standard fragments was performed using HELIOS™ software, though similar operations could be performed on the manufacturer's software. For all those patients wherein a fragment length mutation was identified, a patient report was prepared where the diagnosis was that a VHL mutation was present.

As used in the instant specification and claims, the phrase "standard values for the amplified exon" means the expected length of fragments obtained from amplification of a wild-type gene using the amplification primers in question.

Where no length mutations were detected, it was concluded that the sample contained no detectable length mutation in the VHL tumor suppressor gene. In this case, the quantity of amplification products was compared to the expected quantity, using the amount of amplified control sequence as a means of comparison between samples. Where the ratio of amplified fragment to C4 (control) fragment fell greater than 25% above or below the expected amount, it was concluded that the patients carried a copy number mutation in the VHL tumor suppressor gene. A more detailed explanation of DNA quantity analysis by peak height and area may be found in U.S. patent application Ser. No. U.S. 08/497202, incorporated herein by reference. For all those patients wherein a copy number mutation was identified, a patient report was prepared where the diagnosis was that a VHL mutation was present.

Where no length or quantity mutation was detected, then the patient sample was re-examined using the next level of the hierarchical system.

Level 2: DNA Sequence Analysis

The group of patient samples that proved negative for mutations in the VHL tumor suppressor gene under the fragment length/quantity analysis were re-examined at the next level of the hierarchical system for point mutations in the DNA sequence. This test is highly sensitive and highly specific, but because of its complexity, it is also substantially more expensive than the fragment length/quantity analysis. It was therefore highly advantageous from an overall cost perspective to have avoided the need for testing all patient samples.

DNA from the remaining patients was purified as in the fragment length/quantity analysis, above. Exon containing fragments of the VHL tumor suppressor gene were amplified using primers and conditions listed in the fragment length/quantity analysis, above. However, in order to obtain good sample for sequencing, the primers were not multiplexed, but exon containing fragments were amplified separately. In this case the amplification primers were not labelled with a detectable label.

Once the sets of exons were amplified, DNA sequencing reactions were performed on the amplified sample. Dideoxy sequencing primers have been developed for both strands of each exon of the VHL tumor suppressor gene, and are listed below:

| Name | | Sequence |
| --- | --- | --- |
| vh1-5'X1aseq | [SEQ ID NO:14] | TGGCCTCGCCTCCGTTAC |
| vh1-3'X1aseq | [SEQ ID NO:15] | CCCGCCGTCTTCTTCAGG |
| vh1-5'X1bseq | [SEQ ID NO:16] | AAGAAGACGGCGGGGAGG |
| vh1-3'X1bseq | [SEQ ID NO:17] | CCGTGCTATCGTCCTGCTG |
| vh1-5'X2seq | [SEQ ID NO:18] | GGCTCTTTAACAACCTTT |
| vh1-3'X2seq | [SEQ ID NO:19] | TACCACAACAACCTTATC |
| vh1-5'X3seq | [SEQ ID NO:20] | TTCCTTGTACTGACACCCTA |
| vh1-3'X3seq | [SEQ ID NO:21] | TGCAATGCGCTCCTGTGTCA |

The primers are generally nested inside the amplification primers, i.e. closer to the exon, although in some cases the preferred sequencing primer is in fact the amplification primer. In the format listed above, 5 prime sequencing primer provides the sequence from the sense strand; the 3 prime sequencing primer provides the sequence from the anti-sense strand of the gene. Only one of these primers needs to be used to obtain sequence from the exon in question. The preferred primer for sequencing was conjugated to a fluorescent molecule such as FITC although other forms of detectable labels, including other fluorophores, labeled nucleotides or dideoxynucleotides may be employed.

Dideoxy DNA sequencing was performed using the well known method of Sanger et al., "DNA sequencing with chain terminating inhibitors", Proc. Natl. Acad. Sci USA 74:5463–5467 (1977), as modified for use with Sequenase™ Version 2.0 (Amersham Inc., Cleveland Ohio). Products of the DNA sequencing reaction were analyzed on the Pharmacia A.L.F.™, according to the manufacturer's instructions, as described in the DNA fragment length/quantity analysis, above. HELIOS™ software was used to process the output, and to base-call the patient sample sequence.

Current epidemiological data was used to determine which exon containing fragments are preferably sequenced first. It has been reported that while nearly one-half of identified sporadic mutations occur in exon 2, very few second exon mutations are seen in VHL carrying families (Gnarra et al., supra). Thus, for the biopsy samples being studied, exon 2 is properly the first exon to examine by DNA sequencing. This epidemiological data may change as more patients are studied, in which case the order of exon sequencing may also change.

Samples wherein point mutations were detected relative to the wild-type VHL tumor suppressor gene were recorded and reported to the individual patient's file. Where no mutation was identified, the report stated that no mutation in the VHL tumor suppressor gene could be detected and that the patient's gene corresponded to the wild-type gene. In a commercial setting, the report may be communicated to the patient by electronic transmission or written report, or both.

EXAMPLE 2

In another embodiment of the instant invention, the fragment analysis step of Example 1, supra, is modified as follows.

The amplification primers for fragment length analysis of exon 3, one of which is labelled with a detectable label, are selected to be:

|  | Amplification Primers |
| --- | --- |
| Exon 3 × 5' | CCTCTTGTTCGTTCCTTGTA [SEQ ID NO: 12] |
| Exon 3 × 3' | ACTAAGGAAGGAACCAGTCC [SEQ ID NO: 24] |

These amplification primers are found to be optimally amplified with an annealing temperature of 55° C. When applied to wild-type DNA, the amplified fragment is 370 nt. This fragment is conveniently co-amplified with Exon 1b in fragment analysis pool B2.

| Reaction Pool "B2" | Amplification Primers |
| --- | --- |
| Exon 1b × 5' | GGG CGG AGA ACT GGG ACG AG [SEQ ID NO: 8] |
| Exon 1b × 3' | GGG CGG TAG AGG GGC TTA GA [SEQ ID NO: 9] |
| Exon 3 × 5' | CCTCTTGTTCGTTCCTTGTA [SEQ ID NO: 12] |
| Exon 3 × 3' | ACTAAGGAAGGAACCAGTCC [SEQ ID NO: 24] |
| C4 × 5' control | CTCACCCGCACCTAAGTTT [SEQ ID NO: 22] |
| C4 × 3' control | CCAGGATGAGAGCGGATGGCA [SEQ ID NO: 23] |

The reaction conditions for pool B2 are modified to allow the addition of 50 ng of each of the new primers to the conditions described above as suitable for pool B. Again in this case, the C4 control may be used as it was originally used in pool B. All other conditions remain as they were earlier described.

Multiplexing exons 1b and 3 in the same pool allows the technician to reduce the number of separate reactions required to perform fragment analysis on all the exons.

EXAMPLE 3

In this example, we describe a preferred method of sequencing which is T7 cycle sequencing with thermo sequenase. We set out the protocol below.

A. Preparation of Biotinylated PCR Product for Sequencing

1× Taq polymerase Buffer
(final: 10 mM Tris-HCl, pH 8.3, 50 mM KCl, 1.5 mM MgCl2, 0.001% gelatin)
8 pMol each primer (one of which is biotinylated, the other is normal)
0.2 mM each dNTP
300 ng DNA template
2.5 U Taq DNA polymerase
made up to 25 µl final volume with distilled water
PCR cycle conditions for Perkin Elmer 9600:

| 94° 2 min | ×1 cycle |
| --- | --- |
| 94° 30 sec | |
| 50° 30 sec | ×35 cycles |
| 65° 2 min. | |
| 65° 7 min | ×1 cycle |

* annealling temperature for exon 1a and 1b=55°, exon 2=55° and exon 3=50°

Run 5 µl aliquot on a 1% agarose gel containing ethidium bromide to assess band integrity.

B. Buffer Exchange Using Streptavidin Bead 1. take 8 µl of streptavidin beads (Dynal), wash with 50 µl 2× BW buffer
2. resuspend beads in 10 µl of 2× BW buffer
3. remove 10 µl of PCR product from above and mix with washed beads.
4. sit at RT for 1 hour with periodic mixing by gently tapping side of tube
5. place on magnetic rack, allow PCR bound-beads to separate and remove supernatant. Wash with 50 µl of 1× BW buffer, separate on magnetic rack and remove supernatant. Repeat with 50 µl of TE.
6. resuspend bound beads in 10 µl of distilled water.
7. use 3 µl for cycle sequencing

*2×BW buffer: Binding/Washing buffer; 10 mM Tris pH 7.5/1 mM EDTA/2 M NaCl

C. Cycle Sequencing with Thermo SequenaseO.

Set up following reaction on ice:

2 µl T7 THERMO SEQUENASE® buffer (final: 26 mM Tris-HCl, pH 9.5, 6.5 mM MgCl2)

3 µl of PCR product from above

3 µl (final: ~30 ng/5 pM) Fluoresceinated primer

3 µl distilled water

2 µl diluted T7 THERMO SEQUENASE® enzyme (final 6.4 U)

total volume 13 µl mix well, aliquot 3 µl of above to each of 3 µl A,C,G,T termination tubes (final volume 6 µl)

top with 10 µl mineral oil d/ddA Termination mix contains 750 µM dNTPs, 2.5 µM ddATP d/ddC Termination mix contains 750 µM dNTPs, 2.5 µM ddCTP d/ddG Termination mix contains 750 µM dNTPs, 2.5 µM ddGTP d/ddT Termination mix contains 750 µM dNTPs, 2.5 µM ddTTP Cyle in Perkin Elmer 9600 as follows:

| 94° 2 min | ×1 cycle |
| --- | --- |
| 94° 30 sec | |
| *50° 10 sec | cycle 25 times |
| 70° 30 sec | |
| 70° 2 min | ×1 cycle |

*annealling temperatures for exon 1a, 1b = 55°, exon 2 = 55°, and exon 3 = 50°

D. Run Sequencing Samples.

1. after cycle sequencing reaction is complete, add 6 µl of STOP buffer (dextran blue in formamide)
2. load 6 µl (half of reaction) onto automated sequencer The above described embodiments of the present invention are intended as non-limiting examples of the invention encompassed by the claims below.

What is claimed is:

1. A method for testing a plurality of patients for a disease-associated mutation in the VHL tumor suppressor gene, comprising the steps of:
   a) selecting a hierarchical system of assays comprising at least a first and final assay, said first assay being selected to provide a test for the existence of the disease-associated mutation with less than 1% false results indicating the presence of a disease associated mutation and said final assay being selected to provide a test for the existence of the disease associated mutation with less than 1% false results indicating the presence of a disease associated mutation and less than 1% false results indicating the absence of the disease associated mutation;
   b) analyzing a body sample from each of the plurality of patients using the first assay; and, if the result of the first assay is negative for the presence of a disease-associated mutation;
   c) analyzing the body sample using the final assay.

2. A method according to claim 1 wherein said first assay is a DNA analysis.

3. A method according to claim 1 wherein said final assay is DNA sequencing of at least one exon of the VHL tumor suppressor gene.

4. A method according to claim 1 wherein the hierarchical system of assay techniques is selected from among those techniques which use electrophoretic analysis.

5. A method according to claim 4 wherein the electrophoretic analysis has a resolution of one nucleotide.

6. A method according to claim 1, wherein the hierarchy of assay techniques is selected by a method comprising the steps of:
   a) identifying a plurality of tests for the VHL disease-associated mutation;
   b) determining the sensitivity and specificity for each test by comparing results from tests on a statistically significant plurality of samples against results from tests on the same samples using a test protocol accepted as having a sensitivity and specificity of 100 percent;
   c) defining a outcome mapping matrix containing a plurality of diagnostic test combinations each comprising a combination of tests to be evaluated and assessing the significance of all possible combinations of negative and positive results for the diagnostic test combinations in the matrix;
   d) determining overall sensitivity, overall specificity, overall predictive value of a positive test combination result and overall predictive value of a negative test combination result for at least some of the test combinations in the outcome matrix;

e) determining the estimated cost of testing for those combinations where the overall sensitivity, overall specificity, overall predictive value of a positive test combination result and overall predictive value of a negative test combination result meet a predefined threshold, said predefined threshold defining test combinations with sufficiently high sensitivity and specificity; and f) selecting a diagnostic test combination which has a low estimated cost of testing.

7. A method for testing a plurality of patients for a disease-associated mutation in the Von Hippel-Lindau tumor suppressor gene, comprising the steps of:

a) quantitatively amplifying at least one exon of the Von Hippel-Lindau tumor suppressor gene from a body sample of each of the plurality of patients to produce amplified fragments and comparing the length and quantity of the amplification fragments to standard values based upon the fragments produced by amplification of the same exon in a non-mutant VHL gene; and b) performing a DNA analysis or the disease-associated mutation having a lower level of false results indicating the absence of a mutation than the test of step a on a body sample from each of the plurality of patients that demonstrates the standard values for the amplified exon in the test of step a.

8. A method for testing a plurality of patients for a disease-associated mutation in the Von Hippel-Lindau tumor suppressor gene, comprising the steps of:

a) quantitatively amplifying, from a body sample from each of the plurality of patients, at least one exon of the Von Hippel-Lindau tumor suppressor gene using primers complementary to intron regions flanking each amplified exon;

b) comparing the length of the amplification products for each amplified exon to the length of the amplification products obtained when a wild-type VHL tumor suppressor gene is amplified using the same primers, whereby differences in length between an amplified sample exon and the corresponding amplified wild-type exon reflect the occurrence of an insertion or deletion mutation in the sample Von Hippel-Lindau tumor suppressor gene;

c) determining the nucleic acid sequence of each exon identified in step (b) to contain an insertion or deletion mutation, or in the event no insertion or deletion mutations are identified, the nucleic acid sequence of a least one exon of the Von Hippel-Lindau tumor suppressor gene.

9. A method according to claim 8, further comprising a step before step (c) of determining the quantity of the amplification product and comparing this quantity to that of the corresponding amplified wild-type exon, whereby differences in quantity between an amplified sample exon and the corresponding amplified wild-type exon reflect the occurrence of a mutation in the sample Von Hippel-Lindau tumor suppressor gene.

10. A method according to claim 8, wherein at least two of the exons of the sample Von Hippel-Lindau tumor suppressor gene are coamplified in a single reaction.

11. A method according to claim 10, wherein the primers for the coamplified exons of the Von Hippel-Lindau tumor suppressor gene are selected to provide amplified fragments of different lengths.

12. A method according to claim 8 wherein at least part of exon 1 of the VHL tumor suppressor gene is quantitatively amplified, and wherein the primers used are SEQ ID NO:6 and SEQ ID NO:7.

13. A method according to claim 8 wherein at least part of exon 1 of the VHL tumor suppressor gene is quantitatively amplified, and wherein the primers used are SEQ ID NO:8 and SEQ ID NO:9.

14. A method according to claim 8 wherein at least exon 2 of the Von Hippel-Lindau tumor suppressor gene is quantitatively amplified, and wherein the primers used are SEQ ID NO:10 and SEQ ID NO:11.

15. A method according to claim 8 wherein at least exon 3 of the Von Hippel-Lindau tumor suppressor gene is quantitatively amplified, and wherein the primers used are SEQ ID NO:12 and SEQ ID NO:13.

16. A method according to claim 8 wherein the sequence of the exon is obtained using a primer consisting of a DNA sequence selected from among: SEQ ID NO:14 through SEQ ID NO:21.

17. A method for genetic screening of family members of an individual diagnosed as having Von Hippel-Lindau disease, comprising the steps of:

a) obtaining a body sample from the diagnosed individual;

b) amplifying at least one exon of the Von Hippel-Lindau tumor suppressor gene from the body sample using primers complementary to intron regions flanking each amplified exon;

c) determining the length of the amplification product for each exon amplified and comparing that length to the length or amount of amplification product obtained when a wild-type Von Hippel-Lindau tumor suppressor gene is amplified using the same primers, whereby differences in length between an amplified sample exon and the corresponding amplified wild-type exon reflect the occurrence of an inherited insertion or deletion mutation in the Von Hippel-Lindau tumor suppressor gene of the diagnosed individual; and d) if an inheritable mutation is identified, obtaining body samples from the familial relations of the diagnosed individual; amplifying the exon of the Von Hippel-Lindau tumor suppressor gene found to contain an insertion or deletion mutation in the diagnosed individual in said body samples from the familial relations using the same primers used to amplify the exon in the diagnosed individual; and determining the length of the amplification product for the exon in the amplified familial relation sample and comparing that length to the length of amplification products obtained when the patient sample was amplified, wherein a correlation between the length of the amplified product obtained from the patient sample and the length of the amplified product of a sample from a familial relation is indicative that the relation is a carrier of the mutation.

18. A method according to claim 17, wherein the amplification step is quantitative and further comprising the step of determining the quantity of the amplification products and comparing this quantity to that of the corresponding amplified wild-type exon.

19. A method according to claim 17, further comprising the step of determining the sequence of the exon containing the inherited mutation.

20. A method according to claim 17 wherein at least part of exon 1 of the Von Hippel-Lindau tumor suppressor gene is quantitatively amplified, and wherein the primers used are SEQ ID NO:6 and SEQ ID NO:7.

21. A method according to claim 17 wherein at least part of exon 1 of the Von Hippel-Lindau tumor suppressor gene is quantitatively amplified, and wherein the primers used are SEQ ID NO:8 and SEQ ID NO:9.

22. A method according to claim 17 herein at least exon 2 of the Von Hippel-Lindau tumor suppressor gene is quantitatively amplified, and wherein the primers used are SEQ ID NO:10 and SEQ ID NO:11.

23. A method according to claim 17 wherein at least exon 3 of the Von Hippel-Lindau tumor suppressor gene is quantitatively amplified, and wherein the primers used are SEQ ID NO:12 and SEQ ID NO:13.

24. A method according to claim 6, wherein the estimated cost of testing, $E(C_A)$, is determined using the equation $$E(C_A) = \sum_{r=1}^{n} \left( \rho_{A,r} \sum_{j=1}^{r} C_{(j)} \right)$$

where $\rho_{A,r}$ is the probability that a given test (the r-th test) in the diagnostic test combination, A, will have to be performed to achieve an unambiguous diagnostic result and $C_{(j)}$ is the cost of the j-th test.

* * * * *

SEQUENCE LISTING (1) GENERAL INFORMATION:

(iii) NUMBER OF SEQUENCES: 24

(2) INFORMATION FOR SEQ ID NO: 1:

(i) SEQUENCE CHARACTERISTICS:
         (A) LENGTH: 501
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: intron sequence for VHL (xi) SEQUENCE DESCRIPTION: SEQ ID NO:1:

```
GAATTCAGTT AGTTGACTTT TTGTACTTTA TAAGCGTGAT GATTGGGTGT TCCCGTGTGA      60
GATGCGCCAC CCTCGAACCT TGTTACGACG TCGGCACATT GCGCGTCTGA CATGAAGAAA     120
AAAAAAATTC AGTTAGTCCA CCAGGCACAG TGGCTAAGGC CTGTAATCCC TGCACTTTGA     180
GAGGCCAAGG CAGGAGGATC ACTTGAACCC AGGAGTTCGA GACCAGCCTA GGCAACATAG     240
CGAGACTCCG TTTCAAACAA CAAATAAAAA TAATTAGTCG GGCATGGTGG TGCGCGCCTA     300
CAGTACCAAC TACTCGGGAG GCTGAGGCGA GACGATCGCT TGAGCCAGGG AGGTCAAGGC     360
TGCAGTGAGC CAAGCTCGCG CCACTGCACT CCAGCCCGGG CGACAGAGTG AGACCCTGTC     420
TCCAAAAAAA AAAAAAAACA CCAAACCTTA GAGGGGTGAA AAAAAATTTT ATAGTGGAAA     480
TACAGTAACG AGTTGGCCTA G                                              501
```

(2) INFORMATION FOR SEQ ID NO: 2:

(i) SEQUENCE CHARACTERISTICS:
         (A) LENGTH: 122
         (B) TYPE: nucleic acid
         (C) STRANDEDNESS: double
         (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
         (A) ORGANISM: human (ix) FEATURE:
         (D) OTHER INFORMATION: intron sequence for VHL (xi) SEQUENCE DESCRIPTION: SEQ ID NO:2:

```
AGGTACGGGC CCGGCGCTTA GGCCCGACCC AGCAGGACGA TAGCACGGTC TAAGCCCCTC      60
TACCGCCCCG GGGTCCATTC AGACGGGGAA CTAGGCCCCT TGAGGCAGGA CACATCCAGG     120
GT                                                                   122
```

(2) INFORMATION FOR SEQ ID NO: 3:

(i) SEQUENCE CHARACTERISTICS:
        (A) LENGTH: 118
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: intron sequence for VHL (xi) SEQUENCE DESCRIPTION: SEQ ID NO:3:

```
CTCCTGACCT CTATGATCCG CCTGCCTCGG CCTCCAAAGT GCTGGGATTA CAGGTGTGGG      60

CCACCGTGCC CAGCCACCGG TGTGGGCTCT TTAACAACCT TTGCTTGTCC CGATAGGT       118
```

(2) INFORMATION FOR SEQ ID NO: 4:

(i) SEQUENCE CHARACTERISTICS:
        (A) LENGTH: 167
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: intron sequence for VHL (xi) SEQUENCE DESCRIPTION: SEQ ID NO:4:

```
AGGTACTGAC GTTTTACTTT TTAAAAAGAT AAGGTTGTTG TGGTAAGTAC AGGATAGACC      60

ACTTGAAAAA TTAAGCCCAG TTCTCAATTT TTGCCTGATG TCAGGCACGG TATCCAATCT     120

TTTTGTATCC TATTCTCTAC CATAAATAAA ATGGAAGTGA TGATTTT                  167
```

(2) INFORMATION FOR SEQ ID NO: 5:

(i) SEQUENCE CHARACTERISTICS:
        (A) LENGTH: 235
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: intron sequence for VHL (xi) SEQUENCE DESCRIPTION: SEQ ID NO:5:

CTACAGAAGG CATGAACACC ATGAAGTGTC CATAGGGGCC ACAGCATACA CACTGCCACA    60

TACATGCACT CACTTTTTTT CTTTAACCTA AAAGTGAAGA TCCATCAGTA GTACAGGTAG   120

TTGTTGGCAA AAGCCTCTTG TTCGTTCCTT GTACTGAGAC CCTAGTCTGC CACTGAGGAT   180

TTGGTTTTTG CCCCCTAGTC TGCCACTGAG GATTTGGTTT TTGCCCGTTC CAGTG        235

(2) INFORMATION FOR SEQ ID NO: 6:

(i) SEQUENCE CHARACTERISTICS:
        (A) LENGTH: 24
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
        (A) ORGANISM: human (ix) FEATURE:
        (D) OTHER INFORMATION: amplification primer for VHL (xi) SEQUENCE DESCRIPTION: SEQ ID NO:6:

GGAAATACAG TAACGAGTTG GCCT                                            24

(2) INFORMATION FOR SEQ ID NO: 7:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for VHL (xi) SEQUENCE DESCRIPTION: SEQ ID NO:7:

CCTCCCCGCC GTCTTCTTCA                                                 20

(2) INFORMATION FOR SEQ ID NO: 8:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: amplification primer for VHL (xi) SEQUENCE DESCRIPTION: SEQ ID NO:8:

GGGCGGAGAA CTGGGACGAG                                                  20

(2) INFORMATION FOR SEQ ID NO: 9:

(i) SEQUENCE CHARACTERISTICS:
            (A) LENGTH: 20
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
            (A) ORGANISM: human (ix) FEATURE:
            (D) OTHER INFORMATION: amplification primer for VHL (xi) SEQUENCE DESCRIPTION: SEQ ID NO:9:

GGGCGGTAGA GGGGCTTAGA                                                  20

(2) INFORMATION FOR SEQ ID NO: 10:

(i) SEQUENCE CHARACTERISTICS:
            (A) LENGTH: 19
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
            (A) ORGANISM: human (ix) FEATURE:
            (D) OTHER INFORMATION: amplification primer for VHL (xi) SEQUENCE DESCRIPTION: SEQ ID NO:10:

CACCGGTGTG GGCTCTTTA                                                   19

(2) INFORMATION FOR SEQ ID NO: 11:

(i) SEQUENCE CHARACTERISTICS:
            (A) LENGTH: 22
            (B) TYPE: nucleic acid
            (C) STRANDEDNESS: double
            (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: amplification primer for VHL (xi) SEQUENCE DESCRIPTION: SEQ ID NO:11:

GGGCTTAATT TTTCAAGTGG TC                                                    22

(2) INFORMATION FOR SEQ ID NO: 12:

(i) SEQUENCE CHARACTERISTICS:
              (A) LENGTH: 20
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
              (A) ORGANISM: human (ix) FEATURE:
              (D) OTHER INFORMATION: amplification primer for VHL (xi) SEQUENCE DESCRIPTION: SEQ ID NO:12:

CCTCTTGTTC GTTCCTTGTA                                                       20

(2) INFORMATION FOR SEQ ID NO: 13:

(i) SEQUENCE CHARACTERISTICS:
              (A) LENGTH: 20
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
              (A) ORGANISM: human (ix) FEATURE:
              (D) OTHER INFORMATION: amplification primer for VHL (xi) SEQUENCE DESCRIPTION: SEQ ID NO:13:

TTTGTGATGT TTGCCCCTAA                                                       20

(2) INFORMATION FOR SEQ ID NO: 14:

(i) SEQUENCE CHARACTERISTICS:
              (A) LENGTH: 18
              (B) TYPE: nucleic acid
              (C) STRANDEDNESS: double
              (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:14:

TGGCCTCGCC TCCGTTAC                                                    18

(2) INFORMATION FOR SEQ ID NO: 15:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:15:

CCCGCCGTCT TCTTCAGG                                                    18

(2) INFORMATION FOR SEQ ID NO: 16:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:16:

AAGAAGACGG CGGGGAGG                                                    18

(2) INFORMATION FOR SEQ ID NO: 17:

(i) SEQUENCE CHARACTERISTICS:
             (A) LENGTH: 19
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:17:

CCGTGCTATC GTCCTGCTG                                                  19

(2) INFORMATION FOR SEQ ID NO: 18:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:18:

GGCTCTTTAA CAACCTTT                                                   18

(2) INFORMATION FOR SEQ ID NO: 19:

(i) SEQUENCE CHARACTERISTICS:
             (A) LENGTH: 18
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
             (A) ORGANISM: human (ix) FEATURE:
             (D) OTHER INFORMATION: sequencing primer for VHL (xi) SEQUENCE DESCRIPTION: SEQ ID NO:19:

TACCACAACA ACCTTATC                                                   18

(2) INFORMATION FOR SEQ ID NO: 20:

(i) SEQUENCE CHARACTERISTICS:
             (A) LENGTH: 20
             (B) TYPE: nucleic acid
             (C) STRANDEDNESS: double
             (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
          (A) ORGANISM: human (ix) FEATURE:
          (D) OTHER INFORMATION: sequencing primer for VHL (xi) SEQUENCE DESCRIPTION: SEQ ID NO:20:

TTCCTTGTAC TGAGACCCTA                                              20

(2) INFORMATION FOR SEQ ID NO: 21:

(i) SEQUENCE CHARACTERISTICS:
          (A) LENGTH: 20
          (B) TYPE: nucleic acid
          (C) STRANDEDNESS: double
          (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
          (A) ORGANISM: human (ix) FEATURE:
          (D) OTHER INFORMATION: sequencing primer for VHL (xi) SEQUENCE DESCRIPTION: SEQ ID NO:21:

TGCAATGCGC TCCTGTGTCA                                              20

(2) INFORMATION FOR SEQ ID NO: 22:

(i) SEQUENCE CHARACTERISTICS:
          (A) LENGTH: 19
          (B) TYPE: nucleic acid
          (C) STRANDEDNESS: double
          (D) TOPOLOGY: linear (ii) MOLECULE TYPE: other nucleic acid (iii) HYPOTHETICAL:no (iv) ANTI-SENSE: yes (v) FRAGMENT TYPE: internal (vi) ORIGINAL SOURCE:
          (A) ORGANISM: human (ix) FEATURE:
          (D) OTHER INFORMATION: chromosome 4 amplification control
               primer (xi) SEQUENCE DESCRIPTION: SEQ ID NO:22:

CTCACCCGCA CCTAAGTTT                                               19

(2) INFORMATION FOR SEQ ID NO: 23:

(i) SEQUENCE CHARACTERISTICS:
          (A) LENGTH: 21
          (B) TYPE: nucleic acid -continued

```
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: chromosome 4 amplification control
            primer (xi) SEQUENCE DESCRIPTION: SEQ ID NO:23:

CCAGGATGAG AGCGGATGGC A                                              21

(2) INFORMATION FOR SEQ ID NO: 24:

(i) SEQUENCE CHARACTERISTICS:
        (A) LENGTH: 20
        (B) TYPE: nucleic acid
        (C) STRANDEDNESS: double
        (D) TOPOLOGY: linear (ii) MOLECULE TYPE: other nucleic acid (iii) HYPOTHETICAL:no (iv) ANTI-SENSE: no (v) FRAGMENT TYPE: internal (vi) ORIGINAL SOURCE:
        (A) ORGANISM: human (ix) FEATURE:
        (D) OTHER INFORMATION: amplification primer for VHL (xi) SEQUENCE DESCRIPTION: SEQ ID NO:24:

ACTAAGGAAG GAACCAGTCC                                                20
```